United States Patent
Won et al.

(10) Patent No.: US 9,858,911 B2
(45) Date of Patent: Jan. 2, 2018

(54) TRANSDUCER SUPPORT, ULTRASOUND PROBE, AND ULTRASOUND IMAGING APPARATUS

(71) Applicant: SAMSUNG ELECTRONICS CO., LTD., Suwon-si (KR)

(72) Inventors: Chang Yeon Won, Seoul (KR); Hyun Phill Ko, Seongnam-si (KR); Sung Ki Kim, Seoul (KR); Jeong Mln Na, Seoul (KR); Jae Moon Jo, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 728 days.

(21) Appl. No.: 14/511,511

(22) Filed: Oct. 10, 2014

(65) Prior Publication Data
US 2015/0194143 A1    Jul. 9, 2015

(30) Foreign Application Priority Data

Jan. 6, 2014    (KR) ........................ 10-2014-0001250

(51) Int. Cl.
*G10K 11/00*    (2006.01)
*G10K 11/18*    (2006.01)
(Continued)

(52) U.S. Cl.
CPC .......... *G10K 11/002* (2013.01); *A61B 8/4483* (2013.01); *B06B 1/0685* (2013.01);
(Continued)

(58) Field of Classification Search
CPC .... G01S 7/52079; G01S 7/5208; G01S 15/02; G01S 15/8915; G10K 11/002; G10K 11/18; B06B 1/0685; A61B 8/4483
See application file for complete search history.

(56) References Cited

U.S. PATENT DOCUMENTS

2008/0139945 A1    6/2008  Hu
2011/0208059 A1    8/2011  Cerofolini
(Continued)

FOREIGN PATENT DOCUMENTS

EP          3092822 A1 * 11/2016  ......... G01S 7/52079
JP       2005-218684 A     8/2005
(Continued)

OTHER PUBLICATIONS

International Search Report dated Mar. 26, 2015 in corresponding International Patent Application PCT/KR2012/012583.
(Continued)

*Primary Examiner* — Daniel Pihulic
(74) *Attorney, Agent, or Firm* — Staas & Halsey LLP

(57) ABSTRACT

The present disclosure provides a transducer support, ultrasound probe, and ultrasound imaging apparatus. The ultrasound transducer support includes a first layer having first areas in which heat transfer materials are arranged and second areas in which sound absorbent materials are arranged, the first and second areas being arranged alternately; and a second layer having third areas located below the first areas in which sound absorbent materials are arranged and fourth areas located below the second areas in which heat transfer materials are arranged.

27 Claims, 36 Drawing Sheets

(51) Int. Cl.
*G01S 15/02* (2006.01)
*G01S 7/52* (2006.01)
*G01S 15/89* (2006.01)
*B06B 1/06* (2006.01)
*A61B 8/00* (2006.01)

(52) U.S. Cl.
CPC .......... *G01S 7/52079* (2013.01); *G01S 15/02* (2013.01); *G01S 15/8915* (2013.01); *G10K 11/18* (2013.01); *G01S 7/5208* (2013.01)

(56) References Cited

U.S. PATENT DOCUMENTS

| | | | |
|---|---|---|---|
| 2012/0238880 A1 | 10/2012 | Davidsen | |
| 2015/0061465 A1* | 3/2015 | Lee | B06B 1/06 310/334 |
| 2015/0194143 A1* | 7/2015 | Won | G01S 7/52079 367/7 |
| 2016/0170637 A1* | 6/2016 | Yang | G06F 3/0482 715/773 |
| 2016/0187301 A1* | 6/2016 | Gu | B06B 1/0622 73/644 |

FOREIGN PATENT DOCUMENTS

| | | | | |
|---|---|---|---|---|
| JP | 2009-261840 | | 11/2009 | |
| KR | 10-0781467 B1 | | 12/2007 | |
| KR | 10-1151844 B1 | | 6/2012 | |
| KR | 20150081600 A | * | 7/2015 | ......... G01S 7/52079 |
| WO | WO-2015102277 A1 | * | 7/2015 | ......... G01S 7/52079 |

OTHER PUBLICATIONS

Extended European Search Report dated Jul. 24, 2017 in corresponding European Patent Application No. 14876682.7.

* cited by examiner

TRANSDUCER SUPPORT, ULTRASOUND PROBE, AND ULTRASOUND IMAGING APPARATUS

CROSS-REFERENCE TO RELATED APPLICATIONS

This application claims the benefit under 35 U.S.C. §119(a) of a Korean patent application filed on Jan. 6, 2014 in the Korean Intellectual Property Office and assigned Serial No. 10-2014-0001250, the entire disclosure of which is incorporated hereby incorporated by reference.

BACKGROUND

1. Field

One or more embodiments of the present disclosure relate to a transducer support, and an ultrasound probe and ultrasound imaging apparatus using the transducer support.

2. Description of the Related Art

An imaging apparatus refers to an apparatus for obtaining exterior or interior images of an object using visible rays, infrared rays, ultrasound, radioactive rays, or Nuclear Magnetic Resonance (NMR) or the like. The imaging apparatus may correct the image by adjusting contrast, brightness, or sharpness of a part or the entire of the image as necessary. The imaging apparatus may be e.g., a camera, an ultrasound imaging apparatus, a radiation imaging apparatus, a magnetic resonance imaging apparatus, or the like. The ultrasound imaging apparatus refers to an apparatus for obtaining ultrasound images of an interior part of an object using ultrasound. The ultrasound imaging apparatus may obtain the ultrasound image by receiving ultrasound transmitted from the inside of the object. The ultrasound imaging apparatus may also irradiate ultrasound to the inside of the object and then receive ultrasound reflected from the inside of the object.

SUMMARY

Aspects of the present disclosure are to provide a transducer support having better sound absorbing power and protection against heat, and an ultrasound probe device and ultrasound imaging apparatus using the transducer support.

The present disclosure provides a transducer support, ultrasound probe device and ultrasound imaging apparatus.

In accordance with an aspect of the present invention, provided is a transducer support including: a first layer having first areas in which heat transfer materials are arranged and second areas in which sound absorbent materials are arranged, the first and second areas being arranged alternately; and a second layer having third areas located below the first areas in which sound absorbent materials are arranged and fourth areas located below the second areas in which heat transfer materials are arranged.

The transducer support may further include a third layer having fifth areas located below the fourth areas in which sound absorbent materials are arranged.

The second layer may further include sixth areas located below the first areas in which heat transfer materials are arranged.

The transducer support may further include a third layer having seventh areas located below the sixth areas in which sound absorbent materials are arranged.

The at least one of the first and second layers may have heat transfer materials and sound absorbent materials arranged in multiple columns.

The multiple columns may include a first column in which heat transfer materials and sound absorbent materials are arranged alternately; and a second column in which a sound absorbent material is placed next to a heat transfer material of the first column and a heat transfer material is placed next to a sound absorbent material of the first column.

The transducer support may further include a fourth layer located between the first layer and the second layer, the fourth layer including a heat transfer material.

The sound absorbent materials may be in the shape of a polyhedron, a cylinder, and a cone.

The sound absorbent materials may include at least one of epoxy and hafnium oxides.

The heat transfer absorbent materials may include at least one of graphite, tungsten, tungsten oxide, silicon, aluminum oxide, and glass micro balloon filter.

In accordance with another aspect of the present disclosure, provided is a transducer support including: a first layer in which heat transfer materials and sound absorbent materials are arranged alternately; and a second layer having sound absorbent materials arranged in all or some of areas corresponding to where the heat transfer materials of the first layer are arranged; and heat transfer materials arranged in areas corresponding to where the sound absorbent materials of the first layer are arranged.

The transducer support may further include a third layer having heat transfer materials arranged in all or some of areas corresponding to where the heat transfer materials of the first layer are arranged; and sound absorbent materials arranged in all or some of areas corresponding to where the sound absorbent materials of the first layer are arranged.

In accordance with another aspect of the present disclosure, provided is a transducer support including a main body that transfers heat and includes first and second layers; and a plurality of sound absorbent materials arranged in each of the first and second layers, wherein the plurality of sound absorbent materials are arranged in the first layer in a first pattern and the plurality of sound absorbent materials are arranged in the second layer in a second pattern opposite to the first pattern.

The transducer support may further include a third layer having the plurality of sound absorbent materials arranged in the same pattern as in the first layer.

In accordance with another aspect of the present disclosure, provided is an ultrasound probe including: at least one ultrasound transducer and an ultrasound transducer support on one side of which the at least one ultrasound transducer is mounted, and wherein the ultrasound transducer support including: a first layer having first areas in which heat transfer materials are arranged and second areas in which sound absorbent materials are arranged, the first and second areas being arranged alternately; and a second layer having third areas located below the first areas in which sound absorbent materials are arranged and fourth areas located below the second areas in which heat transfer materials are arranged.

The ultrasound probe may further include a third layer having fifth areas located below the fourth areas in which sound absorbent materials are arranged.

The second layer may further include sixth areas located below the first areas in which heat transfer materials are arranged.

The ultrasound probe may further include a third layer having seventh areas located below the sixth areas in which sound absorbent materials are arranged.

The at least one of the first and second layers may have heat transfer materials and sound absorbent materials arranged in multiple columns.

The multiple columns may include a first column in which heat transfer materials and sound absorbent materials are arranged alternately; and a second column in which a sound absorbent material is placed next to a heat transfer material of the first column and a heat transfer material is placed next to a sound absorbent material of the first column.

The ultrasound probe may further include a fourth layer located between the first layer and the second layer, the fourth layer including a heat transfer material.

The sound absorbent materials may be in the shape of a polyhedron, a cylinder, and a cone.

The sound absorbent materials may include at least one of epoxy and hafnium oxides.

The heat transfer absorbent materials may include at least one of graphite, tungsten, tungsten oxide, silicon, aluminum oxide, and glass micro balloon filter.

In accordance with another aspect of the present disclosure, provided is an ultrasound imaging apparatus including: an ultrasound probe configured to catch ultrasound and output an ultrasound signal corresponding to the ultrasound; and a main body configured to generate an ultrasound image with the ultrasound signal output from the ultrasound probe, wherein the ultrasound probe includes at least one ultrasound transducer and an ultrasound transducer support on one side of which the at least one ultrasound transducer is mounted, and wherein the ultrasound transducer support including: a first layer having first areas in which heat transfer materials are arranged and second areas in which sound absorbent materials are arranged, the first and second areas being arranged alternately; and a second layer having third areas located below the first areas in which sound absorbent materials are arranged and fourth areas located below the second areas in which heat transfer materials are arranged.

In accordance with another aspect of the present disclosure, a transducer support partitioned into multiple layers is provided. The transducer support includes a first layer alternately comprised of first areas in which sound absorbent materials are arranged and second areas in which heat transfer materials are arranged, a second layer alternately comprised of third areas in which sound absorbent materials are arranged and fourth areas in which heat transfer materials are arranged, wherein the locations of the first areas in the first layer correspond with the locations of the fourth areas in the second layer and the locations of the second areas in the first layer correspond with the locations of the third area in the second layer.

In accordance with another aspect of the present disclosure, a transducer support partitioned into multiple layers is provided. The transducer support includes a first layer alternately comprised of first areas in which sound absorbent materials are arranged and second areas in which heat transfer materials are arranged, wherein the locations of the first areas in the first layer are disposed directly above the locations of the fourth areas in the second layer and the locations of the second areas in the first layer are disposed directly above the locations of the third area in the second layer. a second layer alternately comprised of third areas in which sound absorbent materials are arranged and fourth areas in which heat transfer materials are arranged, Other aspects, advantages, and salient features of the disclosure will become apparent to those skilled in the art from the following detailed description, which, taken in conjunction with the annexed drawings, discloses exemplary embodiments of the disclosure

BRIEF DESCRIPTION OF THE DRAWINGS

The above and other features and advantages of the present disclosure will become more apparent by describing in detail exemplary embodiments thereof with reference to the attached drawings in which.

Throughout the drawings, like reference numerals will be understood to refer to like parts, components, and structures.

DETAILED DESCRIPTION

Figure 1:
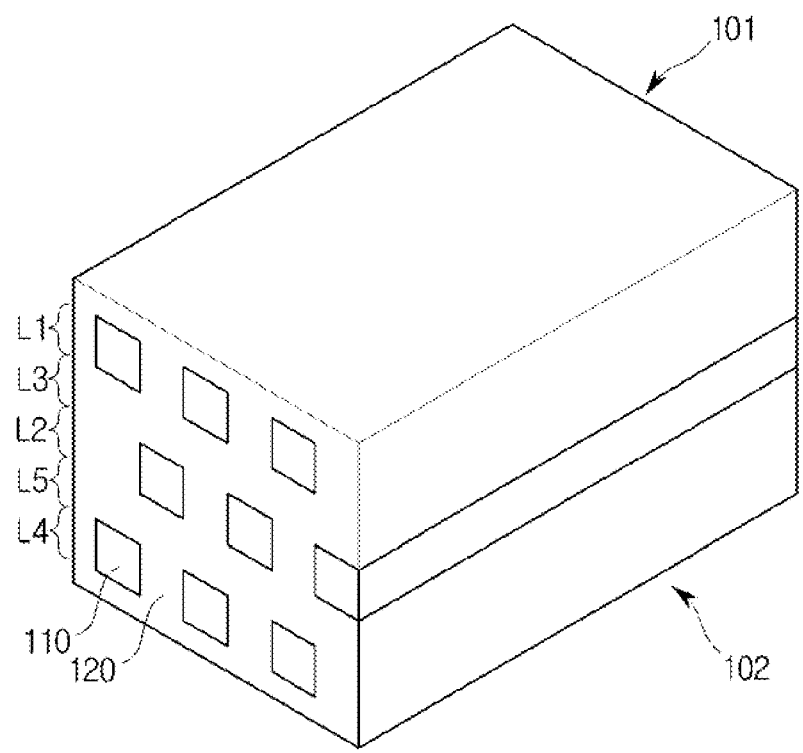
FIGS. 1, 2, 3, and 4 illustrate perspective, front, plane, and side views of a transducer support in accordance with a first embodiment of the present disclosure.

The present disclosure will now be described more fully with reference to the accompanying drawings, in which exemplary embodiments of the disclosure are shown. The disclosure may, however, be embodied in many different forms and should not be construed as being limited to the embodiments set forth herein; rather, these embodiments are provided so that this disclosure will be thorough and complete, and will fully convey the concept of the disclosure to those skilled in the art. Like reference numerals in the drawings denote like elements, and thus their description will be omitted.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present disclosure. The terminology used herein is for the purpose of describing particular embodiments only and is not intended to be limiting of the invention. It is to be understood that the singular forms "a," "an," and "the" include plural references unless the context clearly dictates otherwise.

The term "include (or including)" or "comprise (or comprising)" is inclusive or open-ended and does not exclude additional, unrecited elements or method steps. "Unit", "module", "block", etc. used herein each represent a unit for handling at least one function or operation, and may be implemented in hardware, software, or a combination thereof.

A first embodiment of a transducer support will now be described with reference to FIGS. 1 to 10. FIGS. 1 to 4 illustrate perspective, front, plane, and side views of a transducer support in accordance with a first embodiment of the present disclosure. Although in the embodiment of FIGS. 1 to 4 a transducer support 100 is illustrated in the shape of a hexahedron with top face 101 and bottom face 102, the shape of the transducer support 100 is not limited thereto. The shape of the transducer support 100 may vary depending on an interior shape or structure of an ultrasound probe (or ultrasound probe device), or depending on a demand of the developer. For convenience of explanation, the top face 101 and the bottom face 102 of the transducer support 100 are randomly selected as two opposite sides from among all the faces of the hexahedron, but it will be appreciated that any other two opposite sides of the hexahedron may also be determined as the top and bottom faces 101 and 102.

Referring to FIGS. 1 to 4, the transducer support 100 may include sound absorbent materials 110 and heat transfer materials 120. The sound absorbent materials 110 and the heat transfer materials 120 may be placed between the top and bottom faces 101 and 102 of the transducer support 100.

The sound absorbent materials 110 may absorb sound or ultrasound. The sound absorbent materials 110 may be formed of epoxy resins. The sound absorbent materials 110 may also be formed of hafnium oxides, such as hafnium oxide metal powder. In addition, various other materials that are capable of absorbing sound and ultrasound may be used as the sound absorbent materials 110. According to various embodiments, the sound absorbent materials 110 of the single transducer support 100 may all be formed of epoxy resins or hafnium oxides. Alternatively, some of the sound absorbent materials 110 of the transducer support 100 may be formed of epoxy resins and others may be formed of hafnium dioxides.

The heat transfer materials 120 may release heat to the outside of the transducer support 100 by heat transfer. The heat transferred by the heat transfer materials 120 may be released to the outside of the transducer support 100. The heat transfer materials 120 may be formed of heat-conductive materials. For example, the heat transfer materials 120 may be formed of at least one of graphite, tungsten, tungsten oxide, silicon, aluminum oxide, such as alumina, and glass micro balloon filler. In some embodiments, the heat transfer materials 120 may be formed of any combination thereof. Apart from them, various materials with high heat conductivity may also be used as the heat transfer materials 120.

Figure 3:
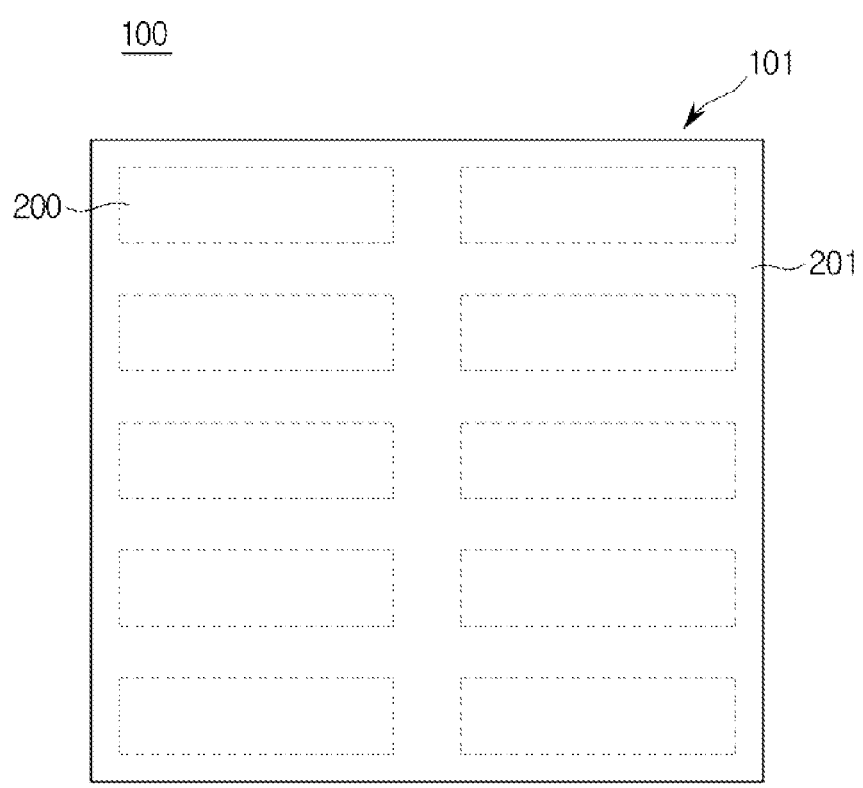

Referring also to FIG. 3, at least one transducer 200, 201 may be mounted on the top face 101 of the transducer support 100. Transducers 200, 201 refer to devices for converting one type of energy to another type. For example, the transducers 200, 201 may convert electrical signals into acoustic energy or vice versa. On the top face 101 of the transducer support 100, transducers may be mounted only in a single column 200 or in a plurality of columns 200 and 201. The transducers 200, 201 mounted on the top face 101 of the transducer support 100 may be ultrasound transducers, for example.

Figure 2:
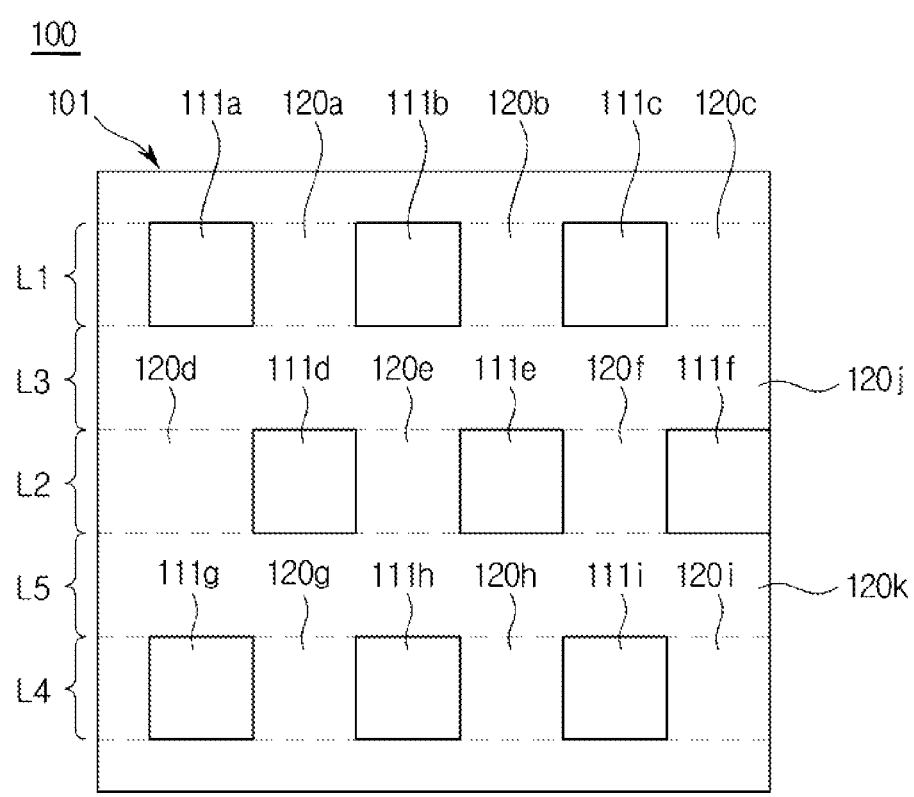
Figure 4:
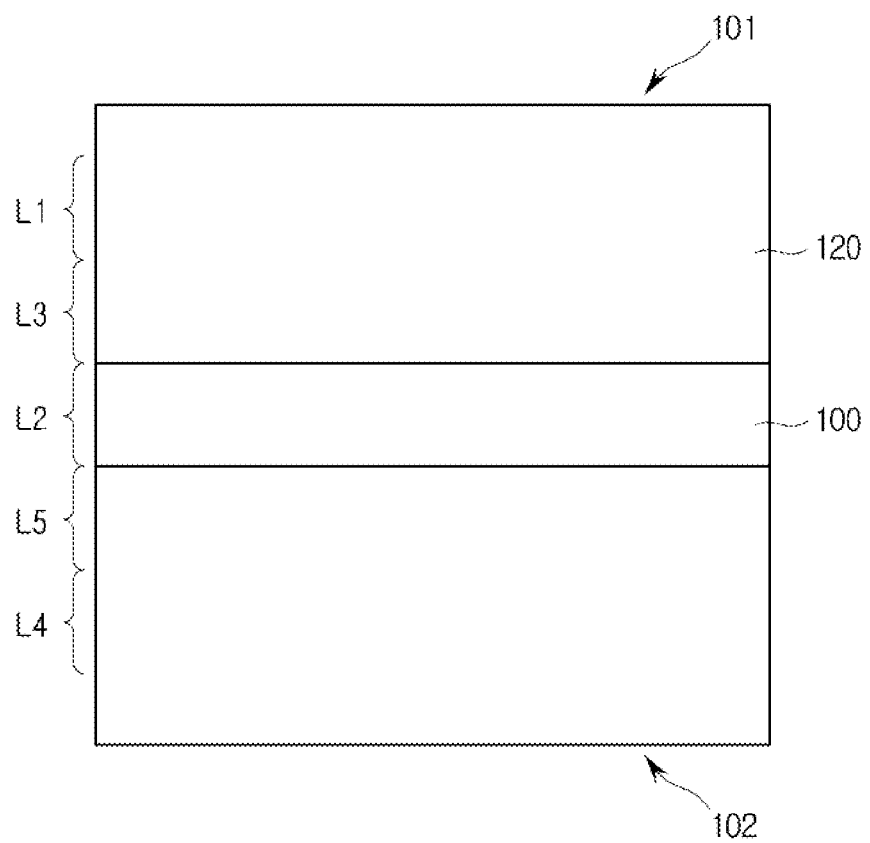

Referring to FIGS. 1, 2, and 4, the transducer support 100 may be partitioned into multiple layers L1 to L5. The partitioning into layers L1 to L5 as used herein are arbitrarily done only for convenience of explanation, but in practice the layers L1 to L5 may not be clearly distinguished within the transducer support 100. The transducer support 100 may include a first layer L1 and a second layer L2. The layers L1 to L5 may be parallel to the top face 101. However, it is not essential that the layers L1 to L5 should be parallel to the top face 101.

The first layer L1 of the transducer support 100 may be next to a top layer on which the transducers 200, 201 may be mounted. The first layer L1 may include first areas in which sound absorbent materials 111a to 111c are arranged, and second areas in which heat transfer materials 120a to 120c are arranged. The sound absorbent materials 111a to 111c may absorb sound or ultrasound generated from the ultrasound transducers 200, 201; and the heat transfer materials 120a to 120c serve as passages through which heat generated from the ultrasound transducers 200, 201 are transferred. The first and second areas may be alternately arranged in the first layer L1. For example, the sound absorbent materials 111a to 111c and heat transfer materials 120a to 120c of the first layer L1 may be alternately arranged as shown in FIG. 2. Specifically, in the first layer L1, a first sound absorbent material 111a is placed, followed by a first heat transfer material 120a, followed by a second sound absorbent material 111a, and so on.

Similarly, the second layer L2 of the transducer support 100 may include third areas in which sound absorbent materials 111d to 111f are arranged and fourth areas in which heat transfer materials 120d to 120f are arranged. Sound absorbent materials 111d to 111f and heat transfer materials 120d to 120f may absorb sound or ultrasound and serve as heat passages, respectively. The sound absorbent materials 111d to 111f in the second layer L2 may be arranged in some or all of the third areas. The heat transfer materials 120d to 120f in the second layer L2 may be arranged in some or all of the fourth areas. The sound absorbent materials 111d to 111f and heat transfer materials 120d to 120f of the second layer L2 may be alternately arranged, as shown in FIGS. 1, 2, and 4.

The arrangement of the sound absorbent materials 111d to 111f and heat transfer materials 120d to 120f in the second layer L2 may be determined depending on the arrangement pattern of the sound absorbent materials 111a to 111c and heat transfer materials 120a to 120c of the first layer L1. Specifically, the arrangement pattern of the sound absorbent materials 111d to 111f of the second layer L2 may be opposite to the arrangement pattern of the sound absorbent materials 111a to 111d of the first layer L1. For example, the heat transfer materials 120d to 120f of the second layer L2 may be arranged in areas corresponding to where the sound absorbent materials 111a to 111c of the first layer L1 are arranged. An area of the second layer L2 corresponding to an area of the first layer L1 refers to an area right below the area of the first layer L1. Accordingly, when the sound absorbent materials 111a to 111c are arranged in particular areas of the first layer L1, the heat transfer materials 120d to 120f may be arranged in areas of the second layer L2, right below the particular areas of the first layer L1. For example, if the first sound absorbent material 111a is arranged on the leftmost part of the first layer L1, a fourth heat transfer material 120d may be arranged on the leftmost part of the second layer L2. The sound absorbent materials 111d to 111f of the second layer L2 may be arranged in areas corresponding to where the heat transfer materials 120a to 120c of the first layer L1 are arranged. When the heat transfer materials 120a to 120c are arranged in particular areas of the first layer L1, the sound absorbent materials 111d to 111f may be arranged in areas of the second layer L2, right below the particular areas of the first layer L1. Accordingly, as shown in FIG. 2, for the first layer L1, the first sound absorbent material 111a may be arranged first in the left-most part, and then heat transfer materials 120a to 120c and the sound absorbent materials 111b, 111c may be alternately arranged; and for the second layer L2, the fourth heat transfer material 120d may be arranged first in the left-most part, and then sound absorbent materials 111d to 111f and the heat transfer materials 120e, 120f may be alternately arranged. As a result, referring to FIG. 2, the sound absorbent materials 111a to 111f may be arranged in a zigzag pattern among the heat transfer materials 120 in the vertical direction of FIG. 2.

The transducer support 100 may further include a fourth layer L4 having sound absorbent materials 111g to 111i and heat transfer materials 120g to 120i. The sound absorbent materials 111g to 111i and heat transfer materials 120g to 120i may be alternately arranged in the third layer L3. The sound absorbent materials 111g to 111i and heat transfer materials 120g to 120i in the fourth layer L4 may be arranged depending on the arrangement pattern of the sound absorbent materials 111d to 111f and heat transfer materials 120d to 120f of the second layer L2. The sound absorbent materials 111g to 111i of the fourth layer L4 may be arranged in fifth areas that correspond to the fourth areas of the second layer L2 in which the heat transfer materials 120d to 120f are arranged. Similarly, the heat transfer materials 120g to 120i of the fourth layer L4 may be arranged in areas that correspond to the third areas of the second layer L2 in which the sound absorbent materials 111d to 111f are arranged.

The transducer support 100 may further include a third layer L3 between the first layer L1 and the second layer L2. The third layer L3 may, as an example, only include heat transfer material 120j. In other words, the third layer L3 may not include any sound absorbent material 110 at all. The thickness of the third layer L3 may or may not be the same as the thickness of the first layer L1 or second layer L2. There may be a fifth layer L5 between the second layer L2 and the fourth layer L4, which also only includes a heat transfer material 120k. The thickness of the fifth layer L5 may or may not be the same as the thickness of any of the first layer L1 to third layer L3.

As a result, referring to FIG. 2, the sound absorbent materials 111a to 111i may be arranged in a zigzag pattern as a whole in the vertical direction of FIG. 2, among the heat transfer material 120.

Figure 5:
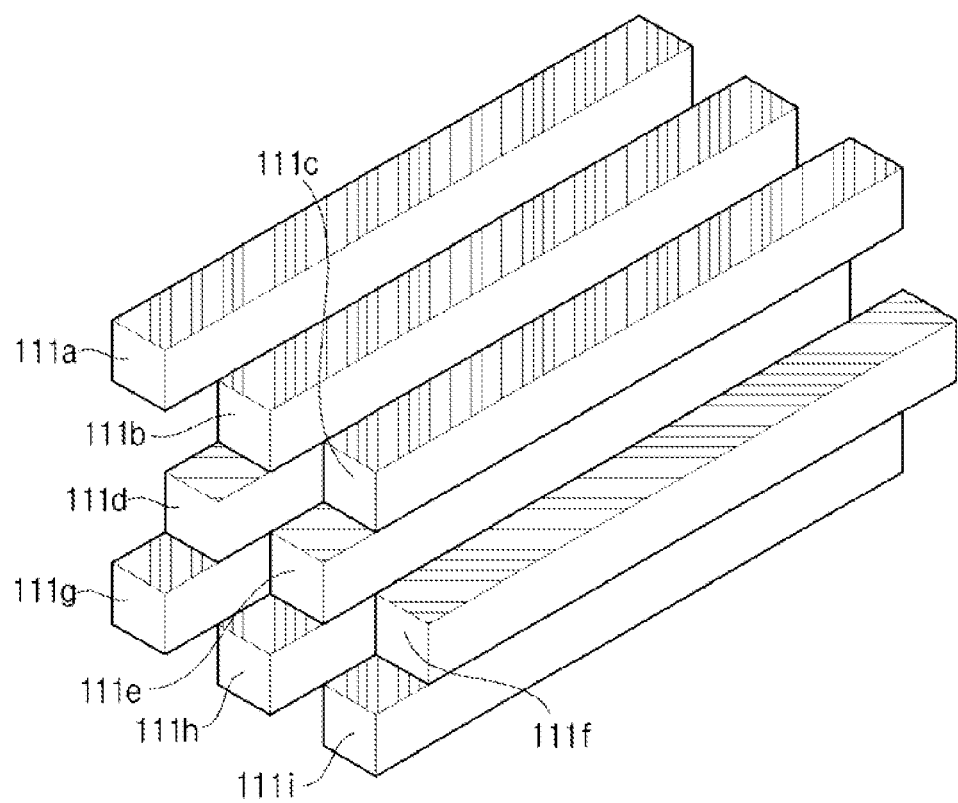
FIGS. 5, 6, 7, and 8 illustrate perspective, front, plane, and side views of an arrangement of sound absorbent materials in the transducer support in accordance with the first embodiment of the present disclosure.
Figure 6:
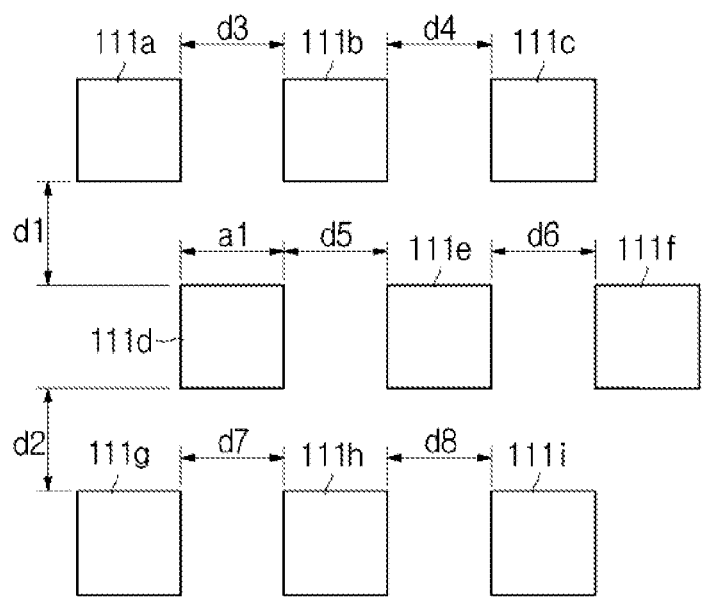
Figure 7:
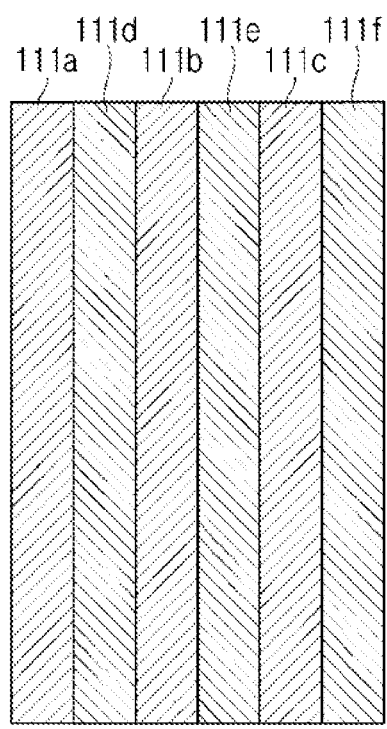
Figure 8:
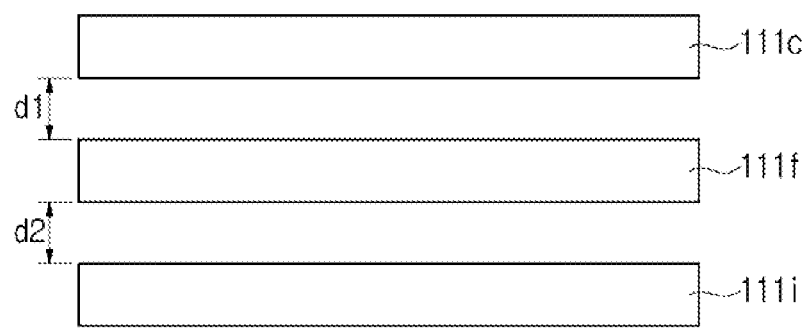

FIGS. 5, 6, 7, and 8 illustrate perspective, front, plane, and side views, respectively, of an arrangement of sound absorbent materials in the transducer support in accordance with the first embodiment of the present disclosure. As discussed above, where the sound absorbent materials 111a to 111i and heat transfer materials 120a to 120k are arranged, the sound absorbent materials 111a to 111i may be arranged in such a form as shown in FIGS. 5, 6, 7, and 8. Referring to FIGS. 5, 6, and 8, the sound absorbent materials 111a to 111i may be spaced apart from each other with some distances d1 to d8. The sound absorbent materials 111a to 111c of the first layer L1 and the sound absorbent materials 111d to 111f of the second layer L2 may be distant from each other as far as the thickness d1 of the third layer L3. Similarly, the sound absorbent materials 111d to 111f of the second layer L2 and the sound absorbent materials 111g to 111i of the fourth layer L4 may be distant from each other as far as the thickness d2 of the fifth layer L5.

Sound absorbent materials in the same layer may also be spaced apart from each other. For example, the sound absorbent materials 111a to 111c of the first layer L1 may be spaced apart from each other with predetermined distances d3 and d4. The distances d3 and d4 between the sound absorbent materials 111a to 111c may be determined depending on the size of each of the heat transfer materials 120a and 120b arranged between the sound absorbent materials 111a to 111c. The distances d3 and d4 may or may not be the same. The distances d3 to d8 between the sound absorbent materials 111a to 111c, 111d to 111f, and 111g to 111i in the respective layers L1, L2, and L3 may or may not be the same. Furthermore, some distances may be the same and others may not be the same. For example, distances d3 and d4 between the sound absorbent materials 111a to 111c of the first layer L1 and distances d7 and d8 between the sound absorbent materials 111g to 111i of the fourth layer L4 may be the same but may be different from distances d5 and d6 between the sound absorbent materials 111d to 111f of the second layer L2. One of the layers L1, L2 or L4 may have distances d3 to d8 between the sound absorbent materials (111a to 111i), narrower than widths of the sound absorbent materials (111a to 111i) of another layer L1, L2 or L4. For example, the distance d3 between the first sound absorbent material 111a and the second sound absorbent material 111b in the first layer L1 may be narrower than width a1 of the sound absorbent material 111d of the second layer L2, which is placed in an area corresponding to where the heat transfer material 120a of the first layer L1 is placed. Similarly, the distances d4 to d8 between sound absorbent materials 111c to 111i may be narrower than widths of the sound absorbent materials 111c to 111i of other layers L2 or L4. As a result, the sound absorbent materials 111a to 111i may be arranged as shown in FIG. 7. Referring to FIG. 7, once the sound absorbent materials 111a to 111i are arranged, ultrasound originated from the ultrasound transducers 200, 201 mounted on the top face 101 of the transducer support 100 and irradiated in the direction of the transducer support 100 may encounter at least one of the plurality of sound absorbent materials 111a to 111i of the transducer support 100 while traveling down to the bottom face 102.

Figure 9:
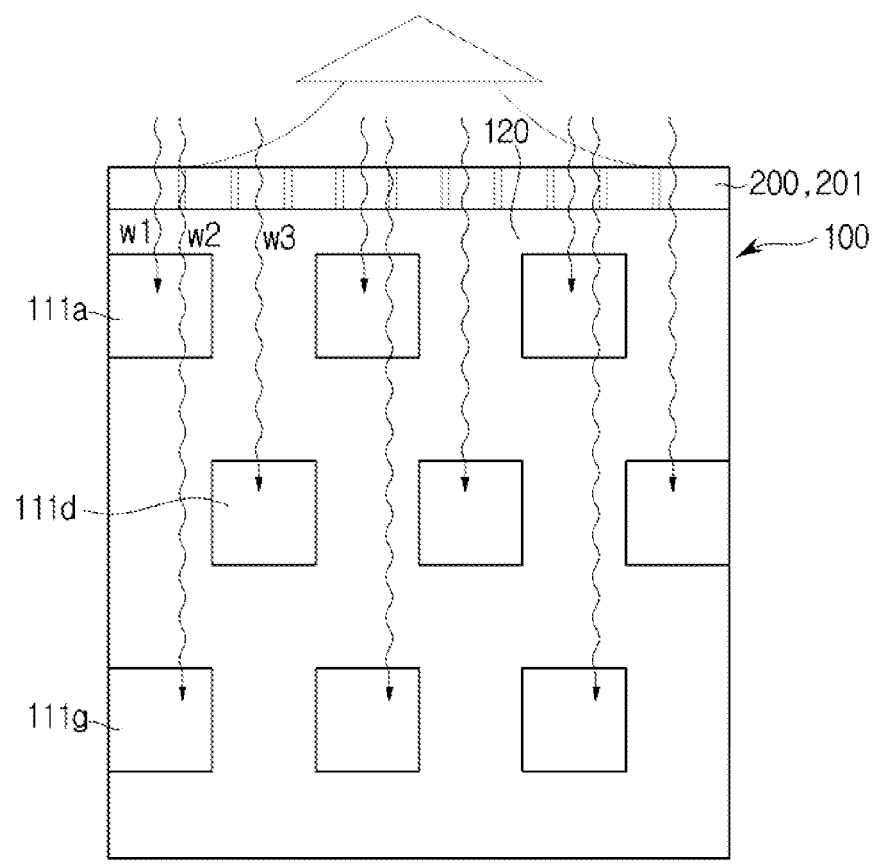
FIG. 9 illustrates how a transducer support absorbs sound.

FIG. 9 illustrates how the transducer support 100 absorbs ultrasound. When powered on, the ultrasound transducers 200, 201 may vibrate at a certain frequency based on the power applied to the respective transducer. Vibration of the ultrasound transducers 200, 201 causes ultrasonic waves w1, w2, and w3 with a frequency corresponding to the vibration frequency of the ultrasound transducers 200, 201, the ultrasonic waves being irradiated in different directions. The ultrasonic waves w1 to w3 irradiated in the direction of the transducer support 110 may enters into the transducer support 100, as shown in FIG. 9. Some ultrasonic waves, e.g., first ultrasonic waves w1 and second ultrasonic waves w2 may reach the first sound absorbent material 111a of the first layer L1. The first sound absorbent material 111a may then absorb the first and second ultrasonic waves w1 and w2. In this regard, all of the ultrasonic waves that have reached the first sound absorbent material 111a, including the first ultrasonic waves w1, may be absorbed by the first sound absorbent material 111a, but in some cases, some of the ultrasonic waves, including the second ultrasonic waves w2 and the third ultrasonic waves w3 may not be absorbed or only a part of the second ultrasonic waves w2 and the third ultrasonic waves w3may be absorbed by the first sound absorbent material 111a. Accordingly, the entire or a part of the second ultrasonic waves w2 and the third ultrasonic waves w3 may penetrate the first sound absorbent material 111a. The second ultrasonic waves w2 that have penetrated the first sound absorbent material 111a may reach the seventh sound absorbent material 111g of the fourth layer L4. The seventh sound absorbent material 111g may absorb the second ultrasonic waves w2. Thus, even if the second ultrasonic waves w2 have penetrated the first sound absorbent material 111a, it may later be absorbed by the seventh sound absorbent material 111g. The third ultrasonic waves w3 may not reach the fourth sound absorbent material 111d. If the third ultrasonic waves w3 reach the fourth sound absorbent material 111d, it may be absorbed by the fourth sound absorbent material 111d. Even if some of the third ultrasonic waves w3 have not been absorbed by the fourth sound absorbent material 111d, it may later be absorbed by a sound absorbent material of a lower layer, as in the case of the first and seventh sound absorbent materials 111a and 111g. As discussed above, ultrasonic waves w1 to w3 irradiated in the direction of the transducer support 100 may encounter a plurality of sound absorbent materials 111a to 111i and then be absorbed by some or all of them while traveling through the transducer support 100 from the top face 101 to the bottom face 102. Accordingly, sound absorbing power of the transducer support 100 may be improved.

Figure 10:
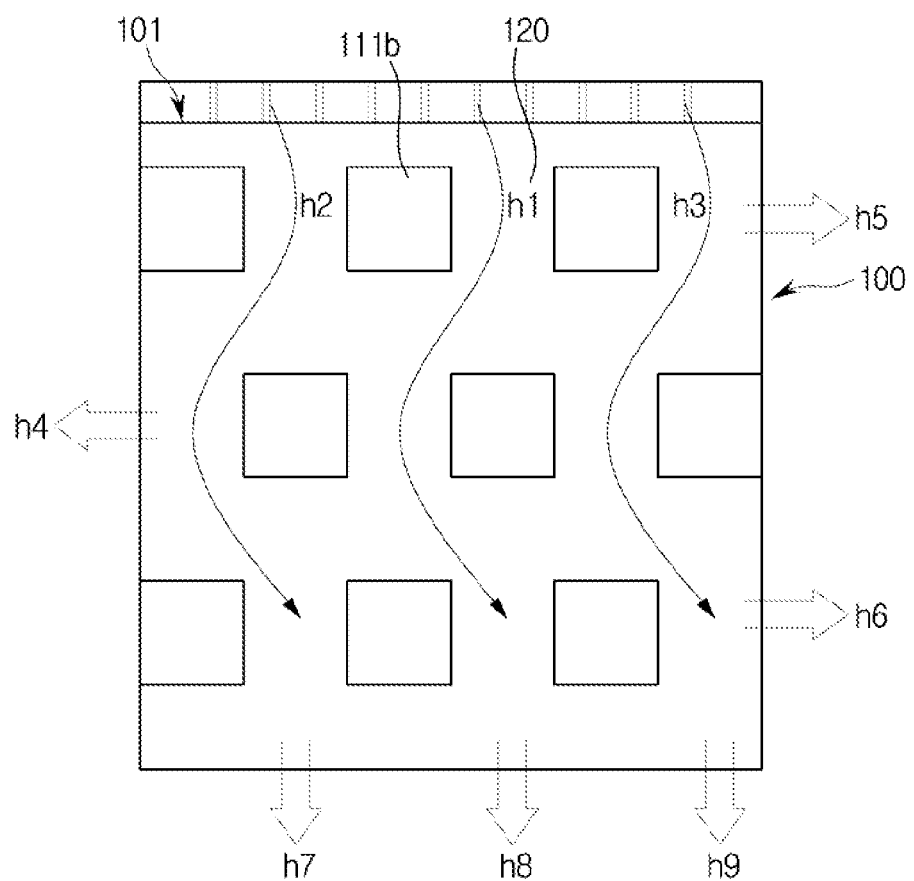
FIG. 10 illustrates how protection against heat works in a transducer support.

FIG. 10 illustrates how protection against heat works in the transducer support 100. When the powered up ultrasound transducers 200, 201 are vibrating, they may generate a great deal of heat. Heat h1 to h3 generated by the ultrasound transducers 200, 201 may be transferred to the transducer support 100. Heat h1 to h3 may be transferred down to the bottom face 102 along the heat transfer materials 120, as shown in FIG. 10. In this regard, heat h1 is transferred along the heat transfer material 120b arranged between the sound absorbent materials 111b and 111c. Part of heat may be released to the outside through the side of the transducer support 100 (h4 to h6) and through the bottom face 102 of the transducer support 100 (h7, h8, and h9).

At least one layer of the plurality of layers L1 to L5 of the transducer support 100, e.g., the first layer L1, the second layer L2, and the fourth layer L4 may include sound absorbent materials 110 and heat transfer materials 120, which may be arranged in a plurality of columns.

Figure 11:
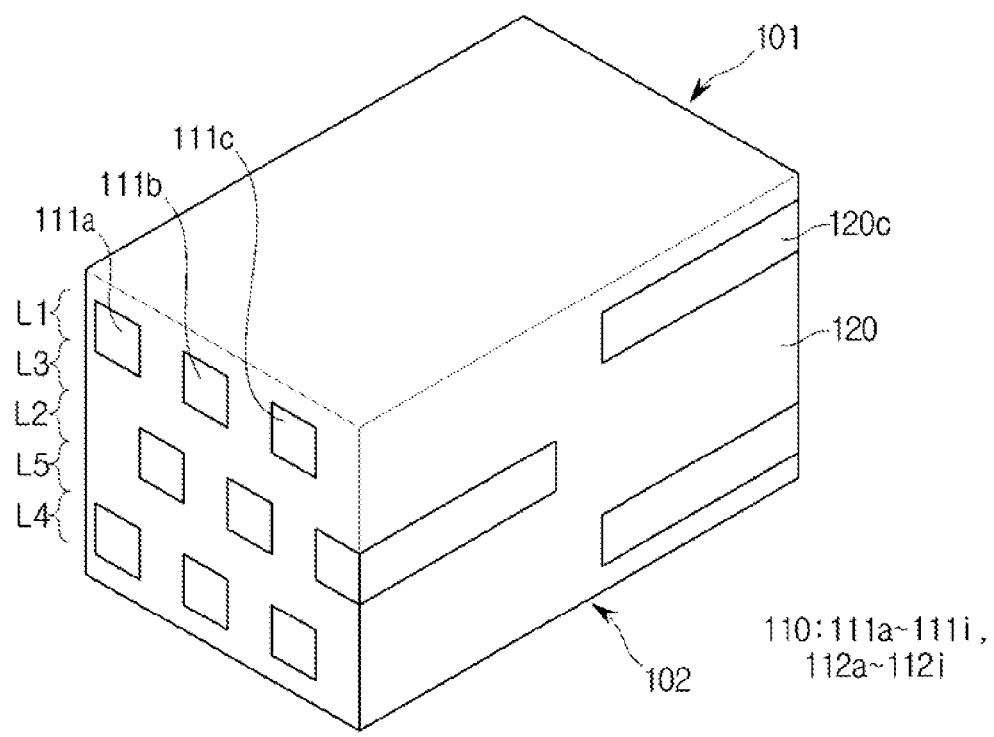
FIGS. 11, 12A and 12B illustrate perspective, front and rear views of a transducer support in accordance with a second embodiment of the present disclosure.
Figure 12A:
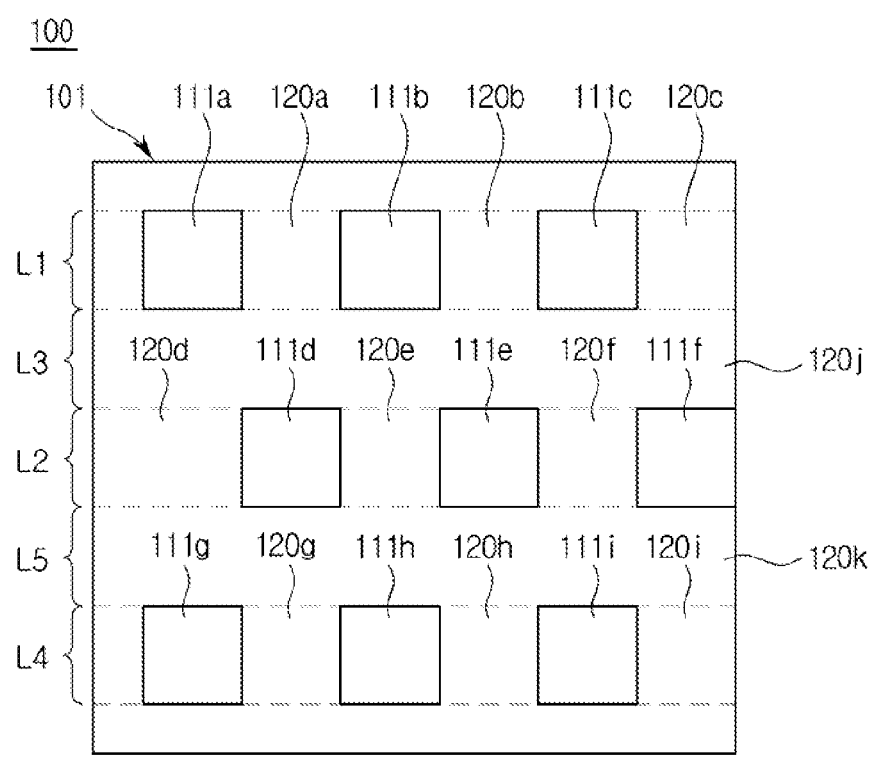
Figure 12B:
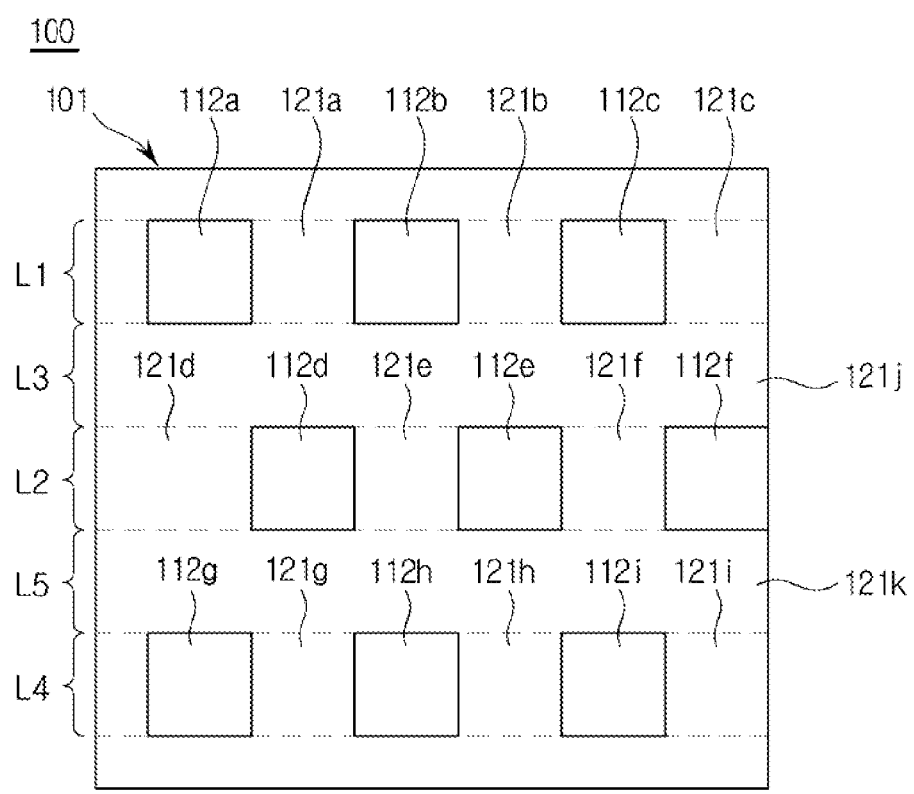

A second embodiment of a transducer support will now be described with reference to FIGS. 11 to 16. FIGS. 11, 12A and 12B illustrate perspective, front and rear views of a transducer support in accordance with a second embodiment of the present disclosure. Referring to FIGS. 11, 12A and 12B, the transducer support 100 may be partitioned into a plurality of layers L1 to L5, among which the first, second, and fourth layers L1, L2, and L4 have sound absorbent materials 110 and heat transfer materials 120 arranged in two columns. The first, second, and fourth layers L1, L2, and L4 may include sound absorbent materials 111a to 111i, 112a to 112i, and 113a to 113i and heat transfer materials, arranged in an alternate form.

Figure 13:
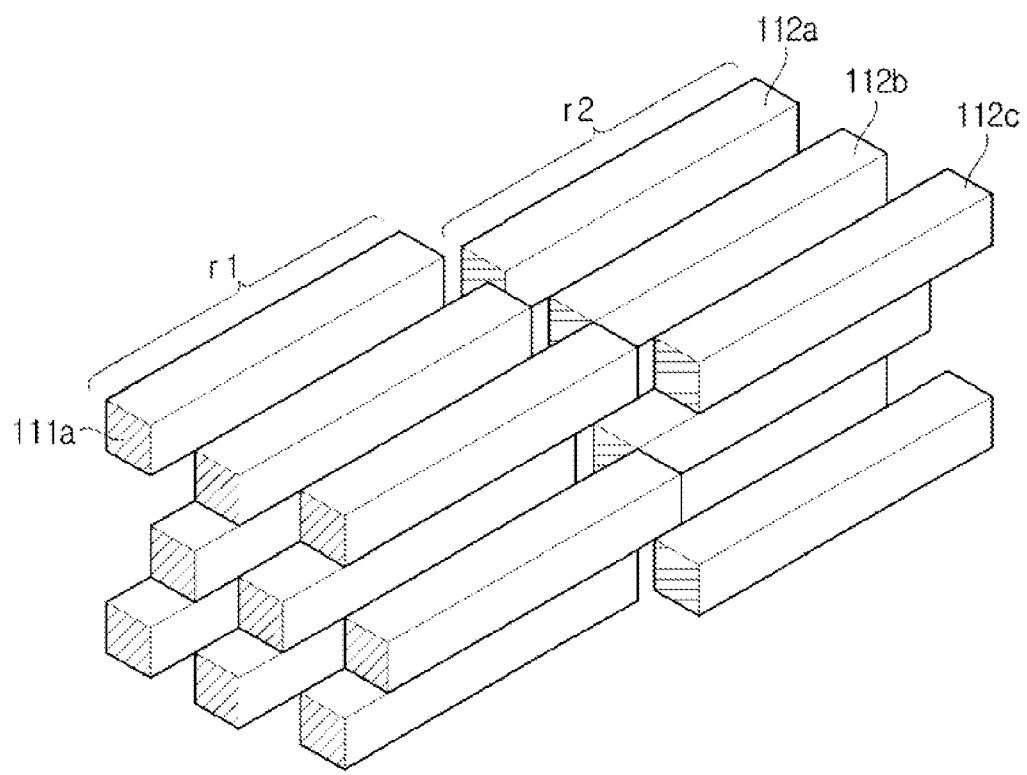
FIGS. 13, 14, 15, and 16 illustrate perspective, front, plane, and side views of an arrangement of sound absorbent materials in the transducer support in accordance with the second embodiment of the present disclosure.
Figure 14:
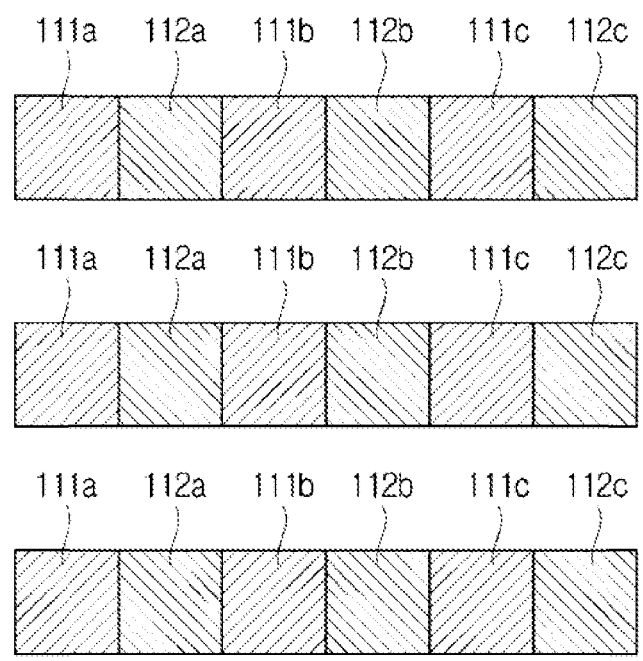
Figure 15:
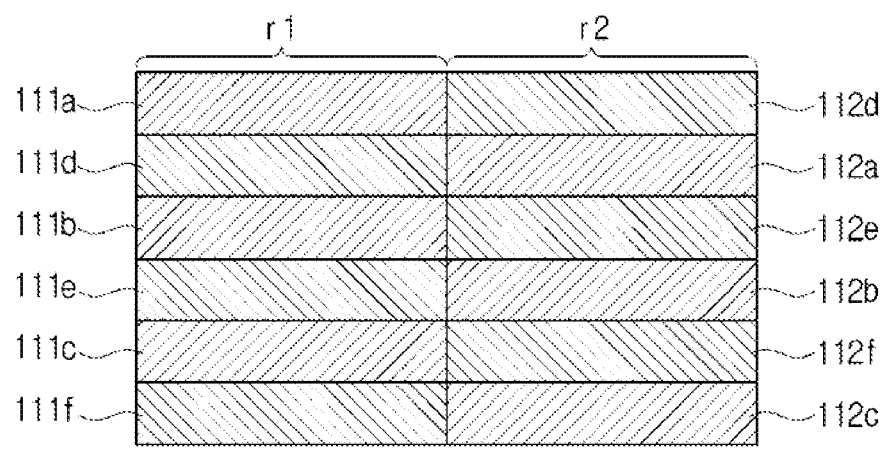
Figure 16:
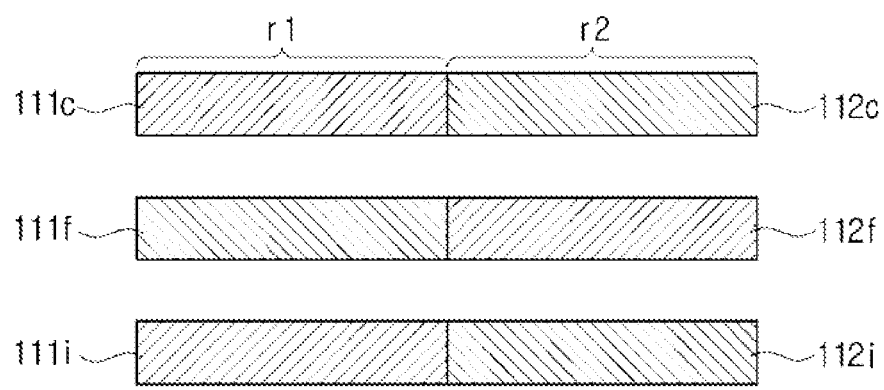

FIGS. 13 to 16 illustrate perspective, front, plane, and side views of an arrangement of sound absorbent materials in the transducer support in accordance with the second embodiment of the present disclosure. As shown in FIGS. 11 to 16, the first layer L1, second layer L2, and fourth layer L4 have sound absorbent materials 111a to 111i, 112a to 112i arranged in two columns r1, r2. The two columns r1, r2 of the sound absorbent materials 111a to 111i, 112a to 112i may be adjacent to each other, or may be some distance apart from each other. For each column r1 or r2, sound absorbent materials 111a to 111i or 112a to 112i may also be spaced apart from each other. Heat transfer materials 120a to 120i may be arranged between the sound absorbent materials 111a to 111i of the first column r1. Similarly, heat transfer materials 121a to 121i may be arranged between the sound absorbent materials 112a to 112i of the second column r2. The sound absorbent materials 111a to 111i of the first column r1 and the sound absorbent materials 112a to 112i of the second column r2 may be alternately arranged in a zigzag pattern, as shown in FIG. 13. Specifically, the heat transfer materials 121a to 121i may be arranged in areas of the second column r2 that correspond to where the sound absorbent materials 111a to 111i of the first column r1 are arranged; and the sound absorbent materials 112a to 112i may be arranged in areas of the second column r2 that correspond to where the heat transfer materials 120a to 120i of the first column r1 are arranged. Accordingly, the sound absorbent materials 111a to 111i of the first column r1 and the sound absorbent materials 112a to 112i of the second column r2 may not be adjacent to each other or only some edges of them may adjoin each other.

The distances between the sound absorbent materials 111a to 111i and 112a to 112i of the columns r1 and r2 in the first, second, and forth layers L1, L2, and L4 may or may not be the same. The distance may be arbitrarily determined. The distances between the sound absorbent materials 111a to 111i, 112a to 112i may be determined depending on the sizes of the heat transfer materials 120a to 120i, 121a to 121i arranged therebetween. The distances between the sound absorbent materials 111a to 111i of the first column r1 in one of the first, second, and fourth layers L1, L2, and L4 may be narrower than the widths of the sound absorbent materials 111a to 111i of the first column r1 in another one of the first, second, and fourth layers L1, L2, and L4. The distances between the sound absorbent materials 112a to 112i of the second column r2 in one of the first, second, and fourth layers L1, L2, and L4 may be narrower than the widths of the sound absorbent materials 112a to 112i of the second column r2 in another one of the first, second, and fourth layers L1, L2, and L4. As a result, the sound absorbent materials 111a to 111i of the first column r1 and the sound absorbent materials 112a to 112i of the second column r2 may be arranged as shown in FIGS. 13 to 16. Accordingly, ultrasound traveling from the top face 101 to the bottom face 102 of the transducer support 100 may encounter at least one of the sound absorbent materials 111a to 111i of the first column r1 and the sound absorbent materials 112a to 112i of the second column r2, and may be absorbed by at least one of the sound absorbent materials 111a to 111i of the first column r1 and the sound absorbent materials 112a to 112i of the second column r2.

In an embodiment, the third layer L3 only formed of heat transfer material 120 may be arranged between the first layer L1 and the second layer L2. In addition, there may be the fifth layer L5 between the second layer L2 and the fourth layer L4, which only includes heat transfer material 120. The third and fifth layers L3 and L5 may serve as heat passages for heat to be transferred to the bottom face 102 or to the side of the transducer support 100.

Figure 17:
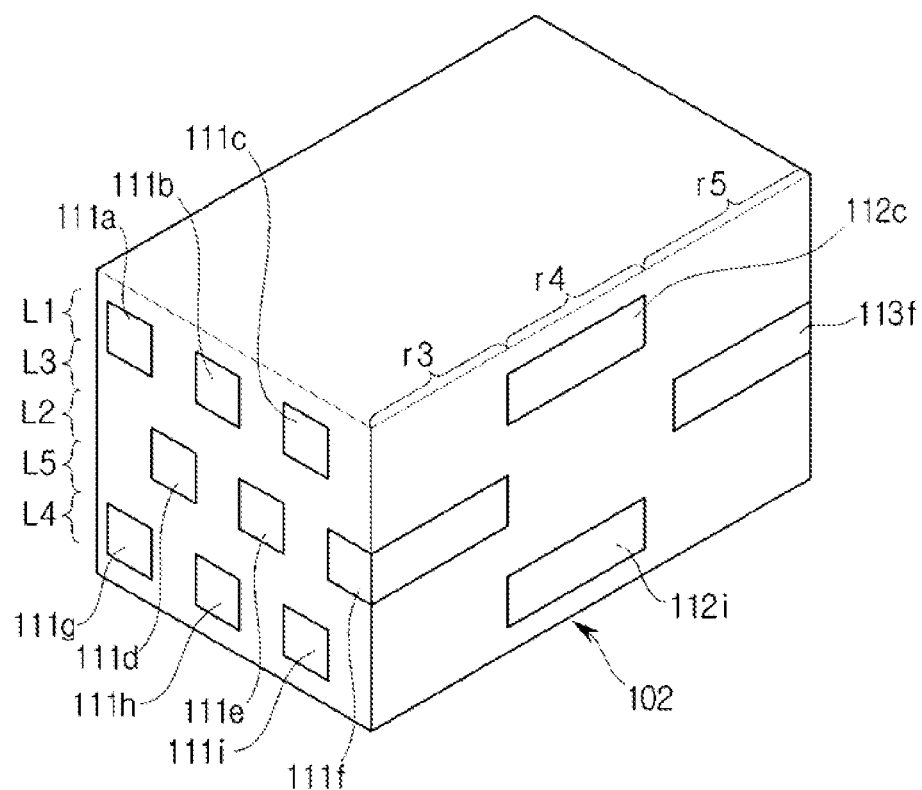
FIGS. 17 and 18 illustrate perspective and plane views of a transducer support in accordance with a third embodiment of the present disclosure.
Figure 18:
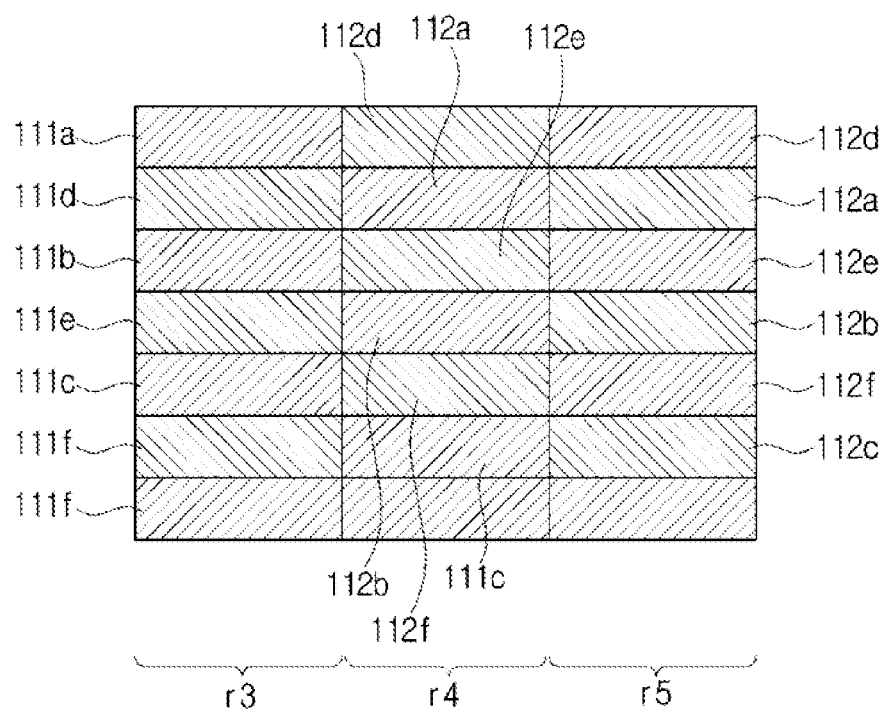

A third embodiment of a transducer support will now be described with reference to FIGS. 17 and 18. FIGS. 17 and 18 illustrate perspective and plane views of a transducer support in accordance with a third embodiment of the present disclosure. Referring to FIGS. 17 and 18, the transducer support 100 may be partitioned into a plurality of layers L1 to L5, at least one e.g., L1, L2, and L4 of which may have sound absorbent materials 110 and heat transfer materials 120 arranged in three columns r3, r4, and r5. As shown in FIG. 17, the first, second, and fourth layers L1, L2, and L4 may include sound absorbent materials 111a to 111i, 112a to 112i, and 113a to 113i and heat transfer materials, arranged in an alternate form. The sound absorbent materials 111a to 111i, 112a to 112i, and 113a to 113i of the first, second, and fourth layers L1, L2, and L4 may be some distance apart from each other, as shown in FIG. 17. In this regard, areas of a fourth column r4 corresponding to areas of a third column r3 in which sound absorbent materials 111a, 111b and 111c are arranged may be absent of sound absorbent materials. In contrast, areas of a fifth column r5 corresponding to areas of the third column r3 in which there are sound absorbent materials 111a, 111 b, and 111c may have sound absorbent materials 113a, 113b, and 113c as in the third column r3. Areas of the fourth column r4 corresponding to areas of the third column r3 in which no sound absorbent material but heat transfer materials 120 are arranged may have sound absorbent materials 112a, 112b, and 112c. In contrast, areas of the fifth column r5 corresponding to areas of the third column r3 in which no sound absorbent material but heat transfer materials 120 are arranged may have no sound absorbent material as in the third column r3. Similarly, areas of the second layer L2 corresponding to areas of the first layer L1 in which sound absorbent materials 111a to 111c, 112a to 112c, and 113a to 113c are arranged may be absent of any sound absorbent material, and areas of the second layer L2 corresponding to areas of the first layer L1 in which sound absorbent materials 111a to 111c, 112a to 112c, and 113a to 113c are not arranged may have sound absorbent materials 111d to 111f, 112d to 112f, and 113d to 113f. Accordingly, within the transducer support 100, sound absorbent materials 111a to 111c, 112a to 112c, and 113a to 113c are not adjacent to each other or some edges of them may adjoin each other. In this regard, the sound absorbent materials 111a to 111i, 112a to 112i, and 113a to 113i may be arranged in a zigzag pattern, as shown in FIGS. 17 and 18. Accordingly, if the ultrasound transducers 200, 201 are mounted on the top face 101 of the transducer support 100, ultrasonic waves output from the ultrasound transducers 200 and 201 may encounter at least one of sound absorbent materials of the first to third columns r1 to r3 and be absorbed by them while traveling down to the bottom face 102.

Similar to what has been described above, third and fifth layers L3 and L5 having heat transfer materials 120 may be arranged between the first and second layers L1 and L2 and the second and fourth layers L2 and L4, respectively. The third and fifth layers L3 and L5 may serve as heat passages for heat to be transferred to the bottom face 102 or to the side of the transducer support 100.

Figure 19:
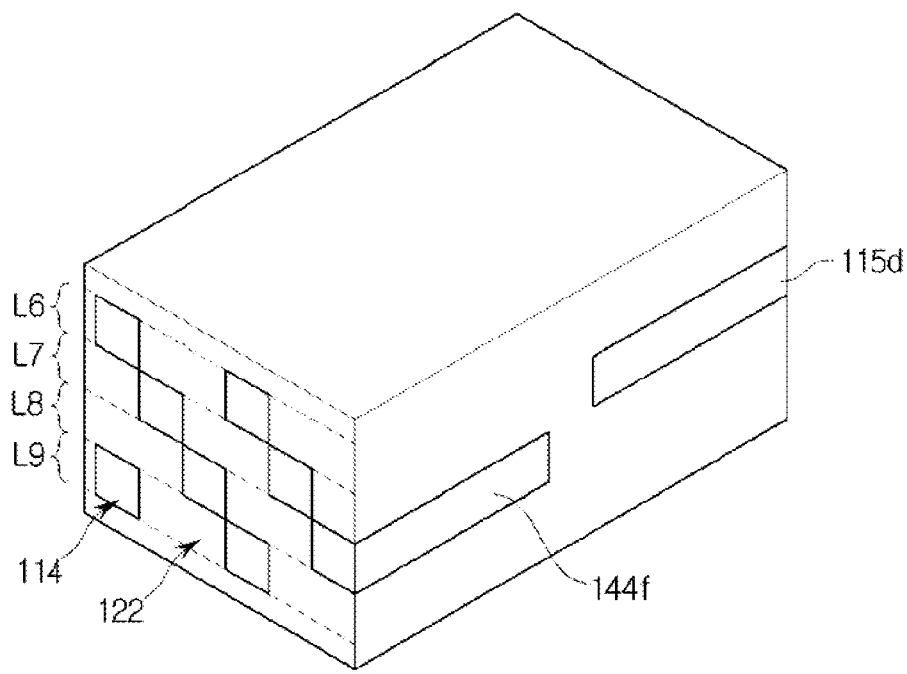
FIGS. 19 and 20 illustrate perspective and front views of a transducer support in accordance with a fourth embodiment of the present disclosure.
Figure 20:
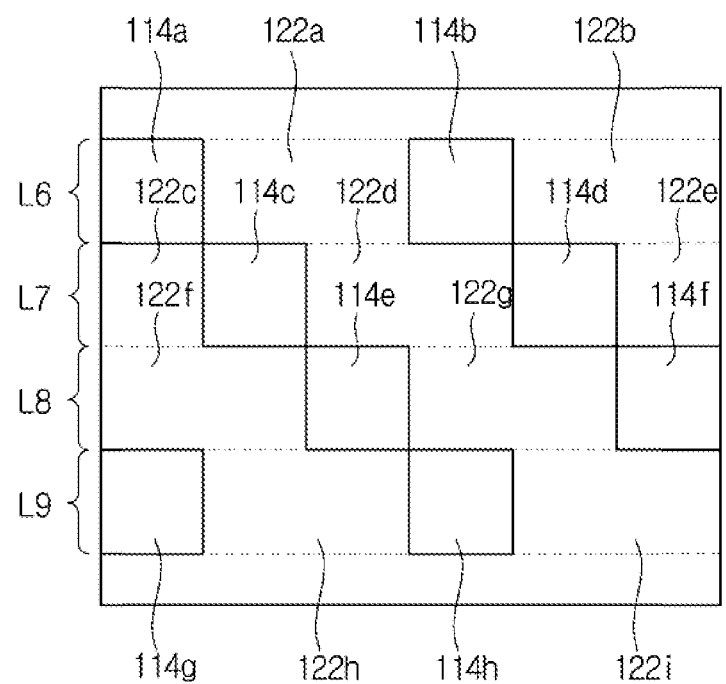

A fourth embodiment of a transducer support will now be described with reference to FIGS. 19 and 20. FIGS. 19 and 20 illustrate perspective and front views of a transducer support in accordance with the fourth embodiment of the present disclosure. Referring to FIGS. 19 and 20, the transducer support 100 may include at least one layer comprised of sound absorbent materials 114a to 114h and heat transfer materials 122a to 12i, e.g., sixth to ninth layers L6 to L9.

Each of the layers L6 to L9 may include sound absorbent materials 114a to 114i, and 115d, and heat transfer materials 122a to 122i. The sound absorbent materials 114a to 114i and 115d and the heat transfer materials 122a to 122i may be alternately arranged. As shown in FIGS. 19 and 20, in the same layer, e.g., in the sixth layer L6, sizes of the sound absorbent materials 114a and 114b and the heat transfer materials 122a and 122b may be different from each other. Sound absorbent materials 114c and 114d of the seventh layer L7 may be arranged in third areas beneath parts of the heat transfer materials 122a and 122b of the sixth layer L6, and heat transfer materials 122c, 122d and 122e of the seventh layer L7 may be arranged in second and sixth areas in which the sound absorbent materials 114c and 114d are not arranged. In other words, the heat transfer materials 122c, 122d and 122e of the seventh layer L7 may be arranged in areas corresponding to the sound absorbent materials 112a and 112b of the sixth layer L6 as well as areas corresponding to parts of the heat transfer materials 122a and 122b.

Sound absorbent materials 114e and 114f of the eighth layer L8 under the sixth and seventh layers L6 and L7 may be arranged in seventh areas corresponding to both the heat transfer materials 122a and 122b of the sixth layer L6 and the heat transfer materials 122d and 122e of the seventh layer L7. The seventh areas may be located below the sixth areas of the seventh layer L7. Heat transfer materials 122f and 122g of the eighth layer L8 may be arranged in areas in which the sound absorbent materials 114e and 114f are not arranged. In other words, the heat transfer materials 122f and 122g may be arranged in an area corresponding to where both the sound absorbent material 114a of the sixth layer L6 and the sound absorbent material 114c of the seventh layer L7 are arranged and an area corresponding to where both the sound absorbent material 114b of the sixth layer L6 and the sound absorbent material 114d of the seventh layer L7 are arranged, respectively.

As a result, sound absorbent materials 114a to 114h may be arranged diagonally within the transducer support 100, as shown in FIG. 19. While the diagonal direction is shown as the bottom right direction in FIG. 19, it may also be bottom left direction in other embodiments. With this arrangement pattern of sound absorbent materials 114a to 114h, ultrasound generated by the ultrasound transducers 200, 201 mounted on the top face 101 of the transducer support 100 may encounter at least one of the sound absorbent materials 114a to 114h and be absorbed by them while traveling down to the bottom face 102. Heat may be transferred by the heat transfer materials 120 each arranged between sound absorbent materials 114a to 114h and released to the outside.

In some embodiments, sound absorbent materials 114a to 114h arranged as shown in FIGS. 19 and 20 may be in two or three or more columns within the transducer support 100 as shown in FIGS. 11 to 18.

Figure 21:
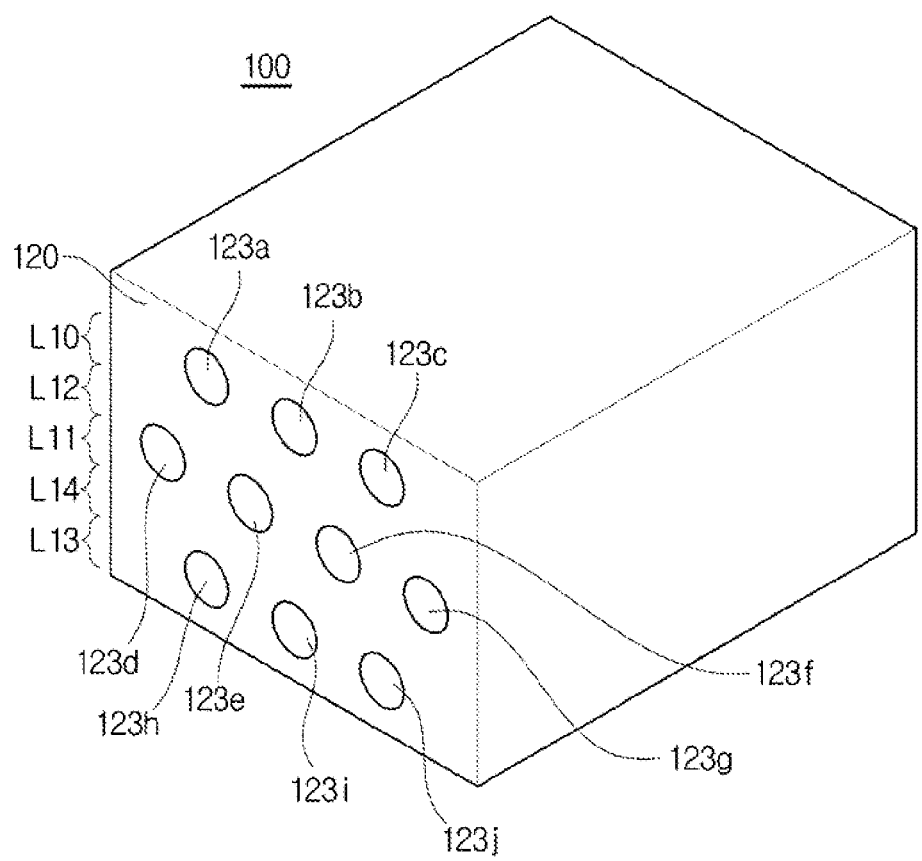
FIGS. 21 and 22 illustrate perspective and front views of a transducer support in accordance with a fifth embodiment of the present disclosure.
Figure 22:
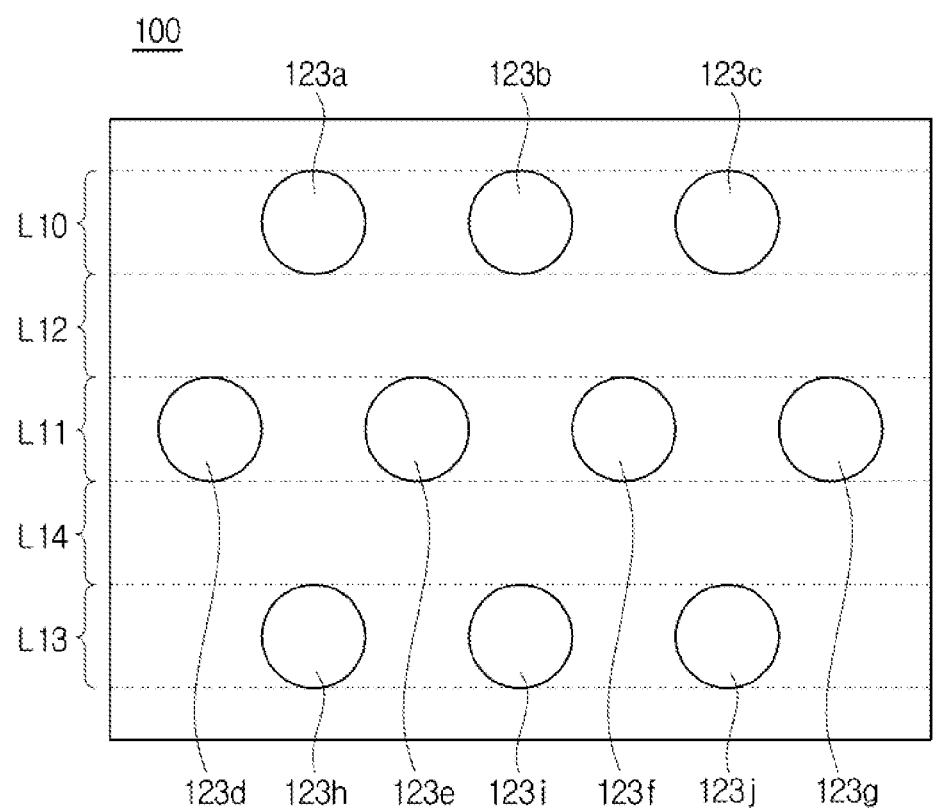
Figure 23:
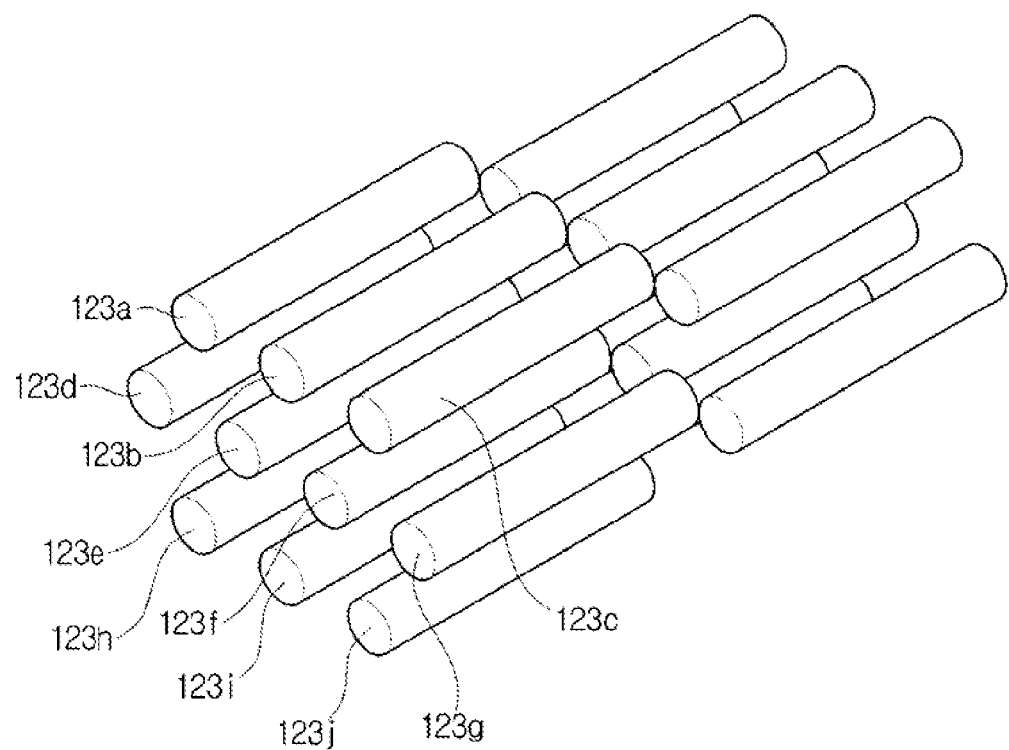
FIGS. 23, 24, 25, and 26 illustrate perspective, front, plane, and side views of an arrangement of sound absorbent materials in the transducer support in accordance with the fifth embodiment of the present disclosure.
Figure 24:
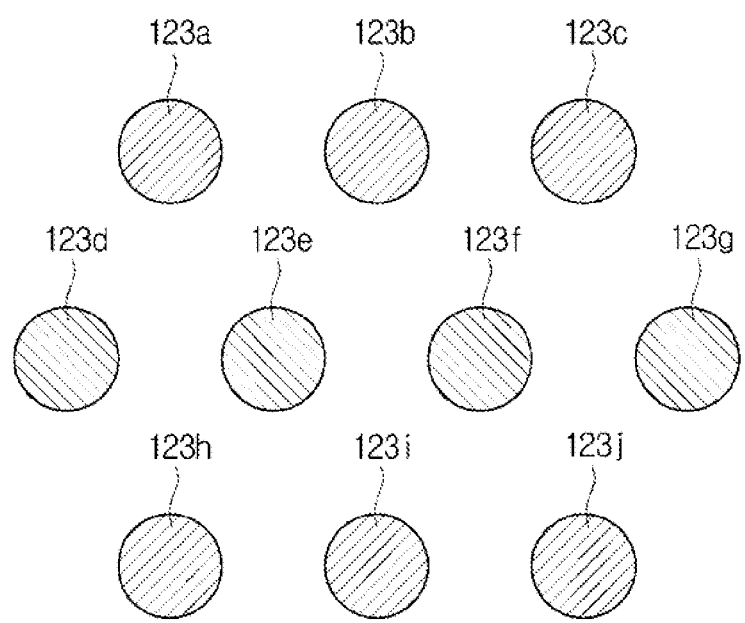
Figure 25:
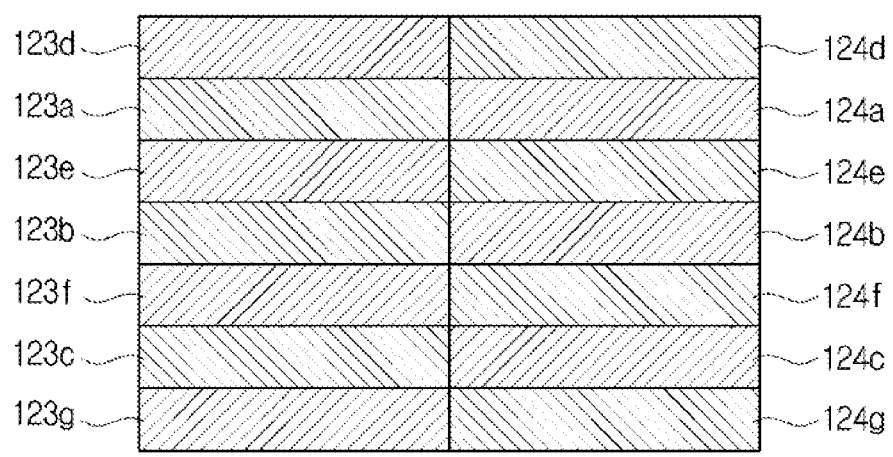
Figure 26:
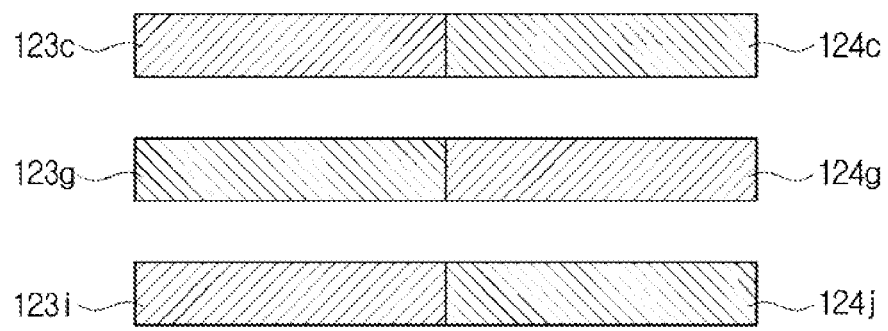

A fifth embodiment of a transducer support will now be described with reference to FIGS. 21 to 26. FIGS. 21 and 22 illustrate perspective and front views of a transducer support in accordance with the fifth embodiment of the present disclosure, and FIGS. 23 to 26 illustrate perspective, front, plane, and side views of an arrangement of sound absorbent materials in the transducer support in accordance with the fifth embodiment of the present disclosure. Referring to FIGS. 21 to 26, sound absorbent materials 123a to 123j included in the transducer support 100 may each be formed in a cylindrical structure. These cylindrically-shaped sound absorbent materials 123a to 123j may be arranged in tenth, eleventh, and thirteenth layers L10, L11, and L13, as shown in FIGS. 21 and 22. Sound absorbent materials of each layer L10, L11, L13 may be spaced some distance apart from each other. There may be heat transfer materials 120 each arranged between the sound absorbent materials 123a to 123j. In any layer, e.g., the tenth layer L10, the distance between the sound absorbent materials 123a to 123c may be shorter than the diameter of the sound absorbent material, e.g., 123d to 133g of the eleventh layer L11. In a layer, e.g., the eleventh layer L11, sound absorbent materials 123d to 123g of the eleventh layer L11 may be arranged in areas corresponding to heat transfer materials 120 of another layer, i.e., the tenth layer L10, each located respectively between sound absorbent materials 123a to 123c. Accordingly, the sound absorbent materials 123a to 123c of the tenth layer L10 and the sound absorbent materials 123d to 123g of the eleventh layer L11 may be arranged in a zigzag pattern, as shown in FIGS. 22 to 24. In an embodiment, sound absorbent materials 123a to 123j and 124a to 124g of the layers L10, L11, and L13 may be arranged in two or more columns, as shown in FIGS. 23, 25, and 26. In this regard, sound absorbent materials 123a to 123j or 124a to 124j of each column may be alternately arranged in a zigzag pattern, as shown in FIG. 25. In this case where the transducer support 100 includes a plurality of layers across which sound absorbent materials 123a to 123j and 124a to 124j are arranged in a zigzag pattern, the sound absorbent materials 123a to 123j and 124a to 124j may absorb the entire ultrasonic waves traveling through the transducer support 100 from the top face 101 to the bottom face 102, thereby increasing sound absorbing power of the transducer support 100.

Twelfth and fourteenth layers L12 and L14, each of which in an embodiment includes only the heat transfer material 120, may be prepared between the tenth and eleventh layers L10 and L11, and eleventh and thirteenth layers L11 and L13, respectively. The twelfth and fourteenth layers L12 and L14 may serve as heat passages for transferring heat radiated from the transducers 200 and 201.

While the sound absorbent material 110 may be shaped like a hexahedron or a cylinder, as shown in FIGS. 1 to 28, their shape is not limited thereto. For example, the sound absorbent material 110 may be in the shape of a polyhedron, such as a tetrahedron or a pentahedron, or in the shape of a cone or a pyramid. Furthermore, the sound absorbent material 110 may have a prism-like shape, such as a pentagonal prism. In addition, the sound absorbent material may be implemented in a variety of other shapes not listed herein.

Figure 27:
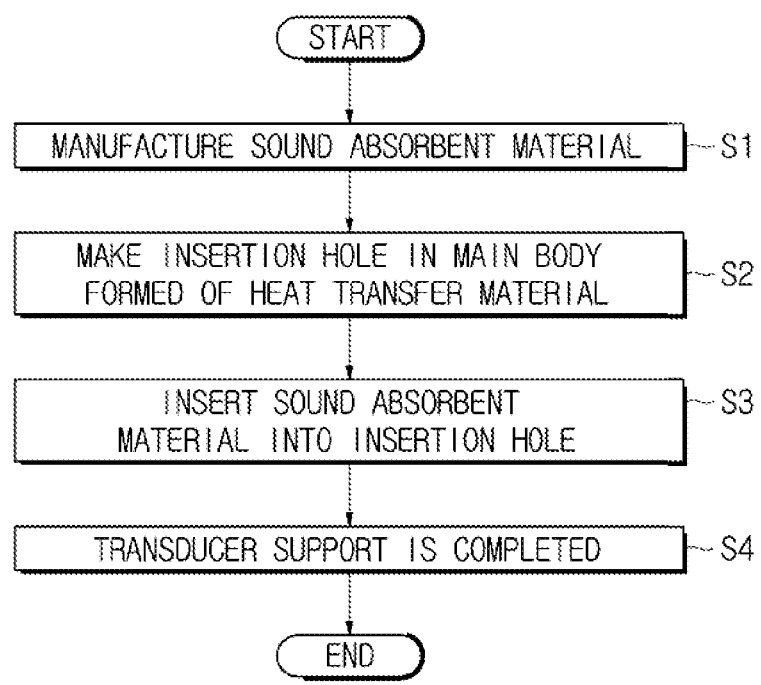
FIG. 27 is a flowchart illustrating an embodiment of a manufacturing process of a transducer support.

An embodiment of a manufacturing process of a transducer support will now be described in connection with FIGS. 27 and 28. FIG. 27 is a flowchart illustrating an embodiment of a manufacturing process of a transducer support, and FIG. 28 illustrates an embodiment of a manufacturing process of a transducer support.

Figure 28:
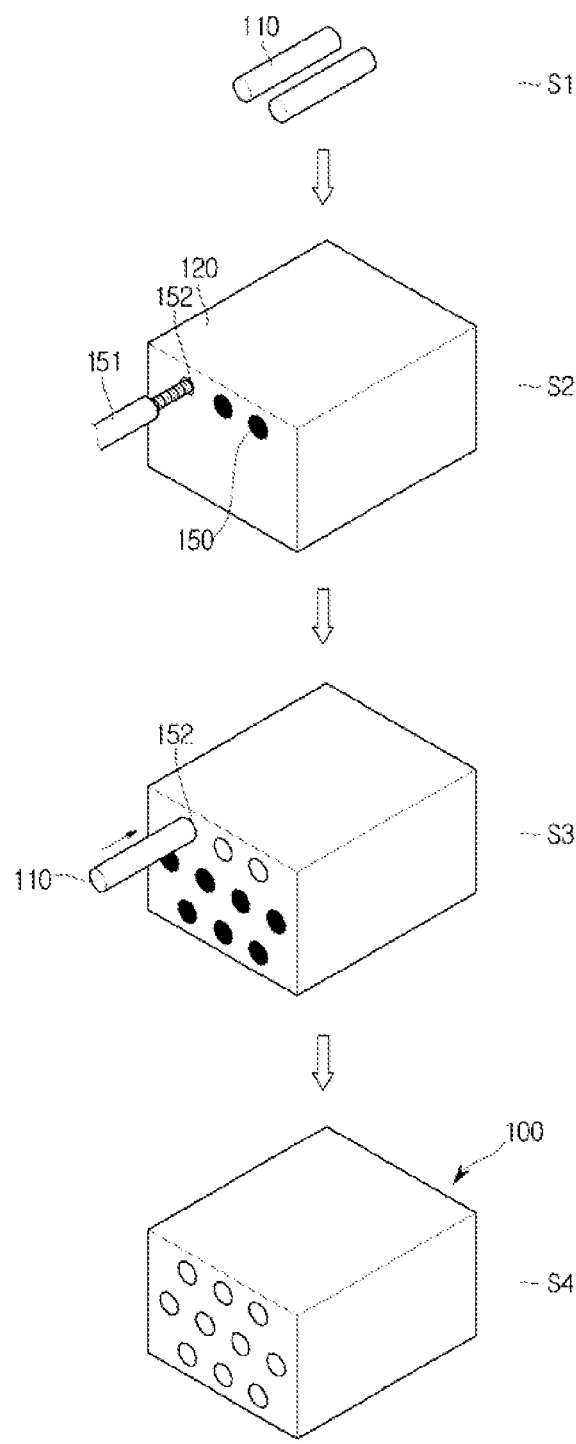
FIG. 28 illustrates an embodiment of a manufacturing process of a transducer support.

Referring to FIGS. 27 and 28, the manufacturing process of a transducer support begins by preparing or manufacturing the sound absorbent materials 110 in a predetermined shape, such as a hexahedron or a cylinder, in operation s1. Next, at least one insertion hole, such as insertion holes 150 and 152, into which the sound absorbent materials 110 may be inserted, may be made in the heat transfer material 120 using a drilling device 151, such as a drill or gimlet, in operation s2. The operations s1 and s2 may be performed in the opposite sequence, or may be performed simultaneously. The insertion holes 150 and 152 may be formed through the heat transfer material 120 from one side to the other side, or may be formed from one side to the middle of the heat transfer material 120. Furthermore, the insertion holes 150 and 152 may start from one side of the heat transfer material 120 or start from multiple sides of the heat transfer material 120. The shape of the insertion holes 150 and 152 may or may not be the same. Once the insertion holes 150 and 152 are made in the heat transfer material 120, the sound absorbent materials 110 of a predetermined shape may be inserted into the insertion holes 150 and 152, in operation s3. The sound absorbent materials 110 to be inserted into the insertion holes 150 and 152 may or may not be the same. Also, the shape of the sound absorbent materials 110 to be inserted into the insertion holes 150 and 152 may or may not be the same. As such, the transducer support 100 may be completed, in operation s4. An additional operation of cutting the heat transfer material 120 having the sound absorbent materials 110 inserted thereto to be inserted into an ultrasound probe may further be performed. In some embodiments, the transducer support 100 may be manufactured by injecting a liquid (or a solid or gel) type of sound absorbent materials into the insertion holes 130 and solidifying them.

Figure 29:
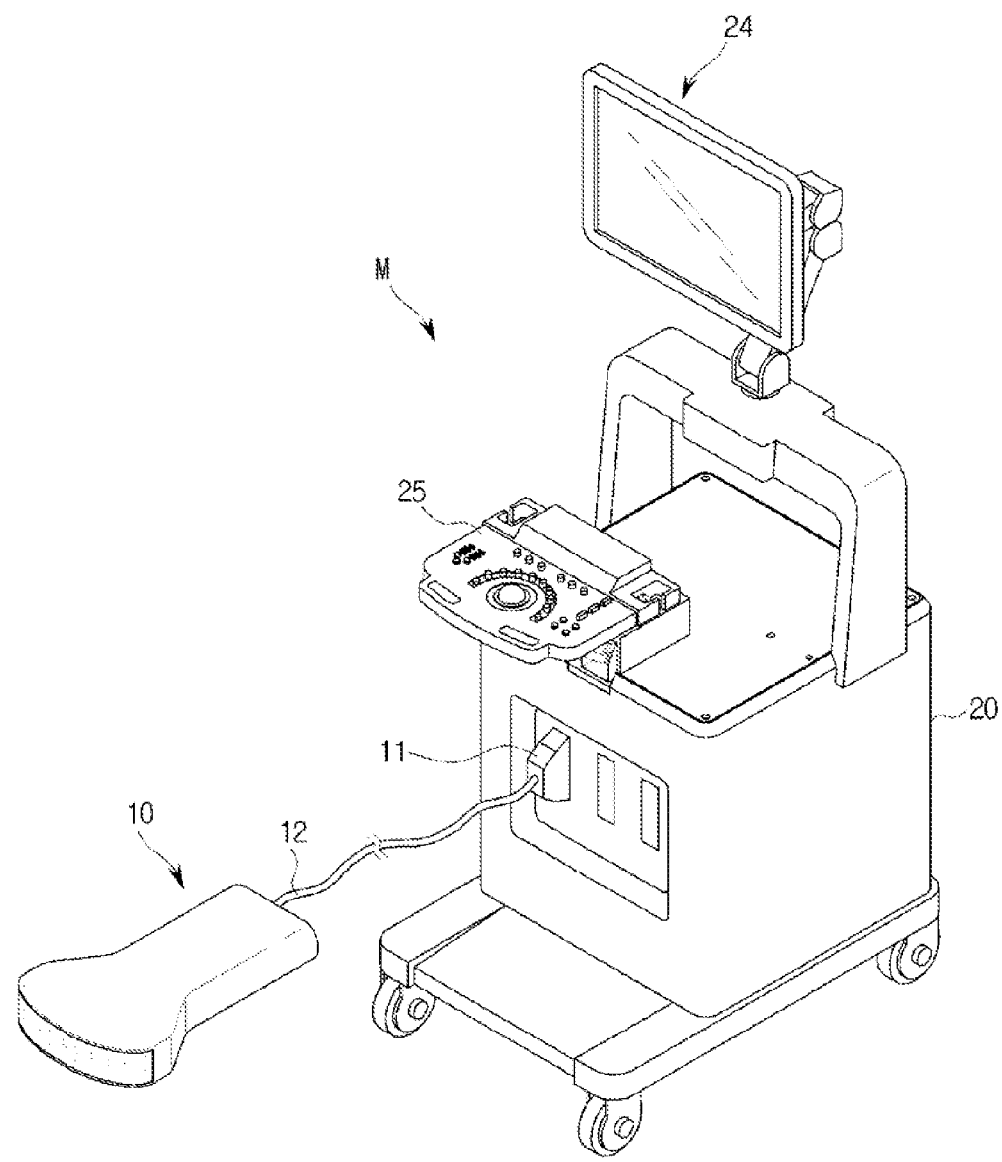
FIG. 29 illustrates an embodiment of an ultrasonic apparatus.
Figure 30:
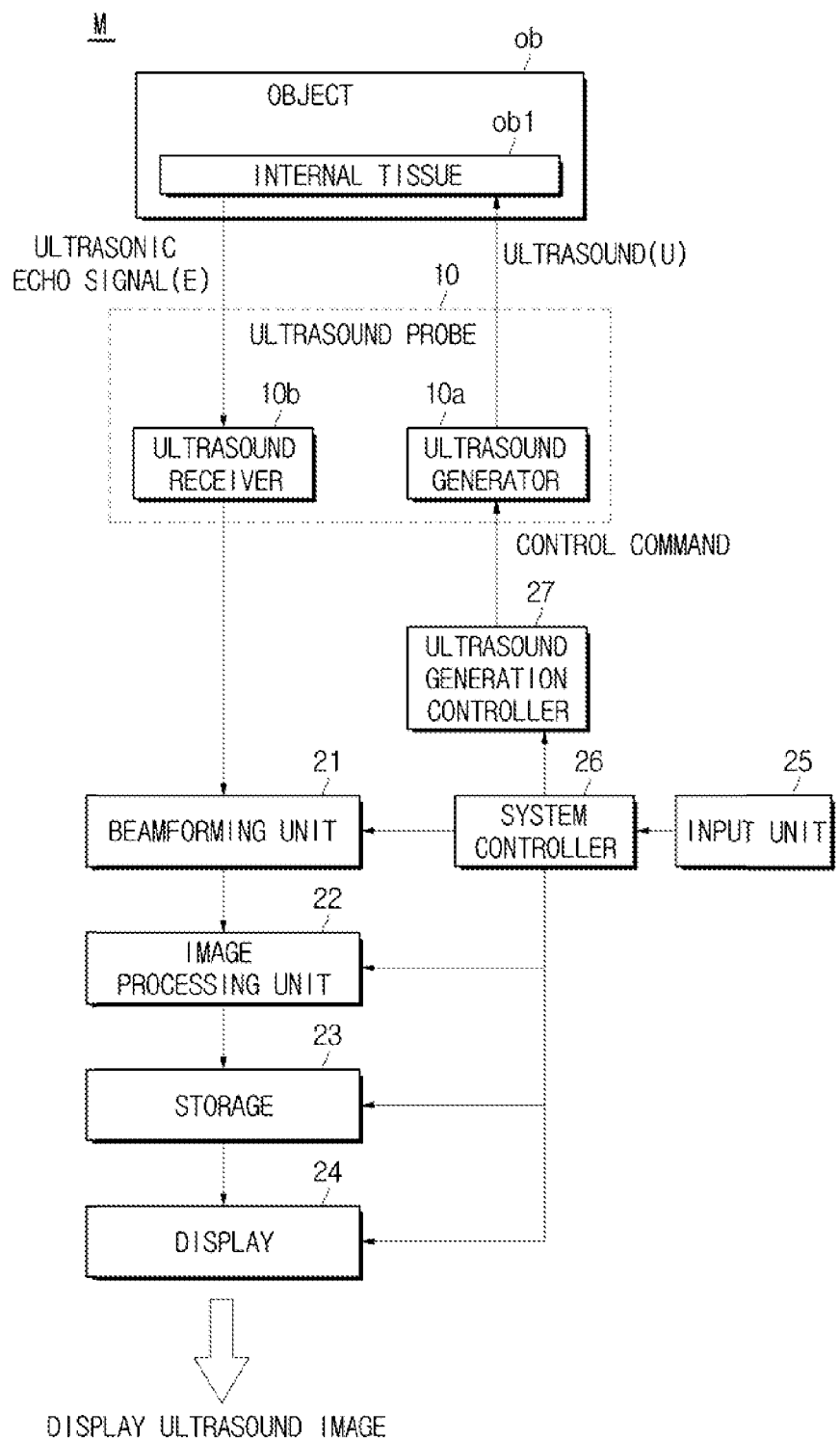
FIG. 30 is a block diagram of an embodiment of an ultrasonic apparatus.

An ultrasound imaging apparatus will now be described in connection with FIGS. 29 to 35. FIG. 29 illustrates an embodiment of an appearance of an ultrasound imaging apparatus, and FIG. 30 is a block diagram of an embodiment of the ultrasound imaging apparatus. Referring to FIG. 29, an ultrasound imaging device M may include an ultrasound probe 10 (or ultrasound probe device) and a main body 20.

The ultrasound probe 10 may receive ultrasound irradiated from inside an object such as a patient and convert the ultrasound to electrical ultrasound signals. In this regard, referring also to FIG. 30, the ultrasound probe 10 may generate ultrasound U with a certain frequency and irradiate the ultrasound U to a target part ob1 inside an object ob. The ultrasound probe 10 may be at least one of a linear array probe, a convex array probe, a sector phased array probe, and a mechanical sector array probe. The ultrasound probe 10 may include an ultrasound generator 10a and an ultrasound receiver 10b. The ultrasound generator 10a may generate ultrasound under a control command sent from an ultrasound generation controller 27, and may irradiate the ultrasound to the target part ob1 of the object ob. The ultrasound receiver 10b may receive ultrasonic echo signals E bounced off the target part ob1 or generated by e.g., a laser in the target part ob1, and convert the ultrasonic echo signals E to electrical ultrasound signals. The ultrasound generator 10a and the ultrasound receiver 10b may be ultrasound transducers. In some embodiments, the ultrasound probe 10 may include an ultrasound transceiver (not shown), which is an ultrasound transducer that both generates and receives ultrasound.

Figure 31:
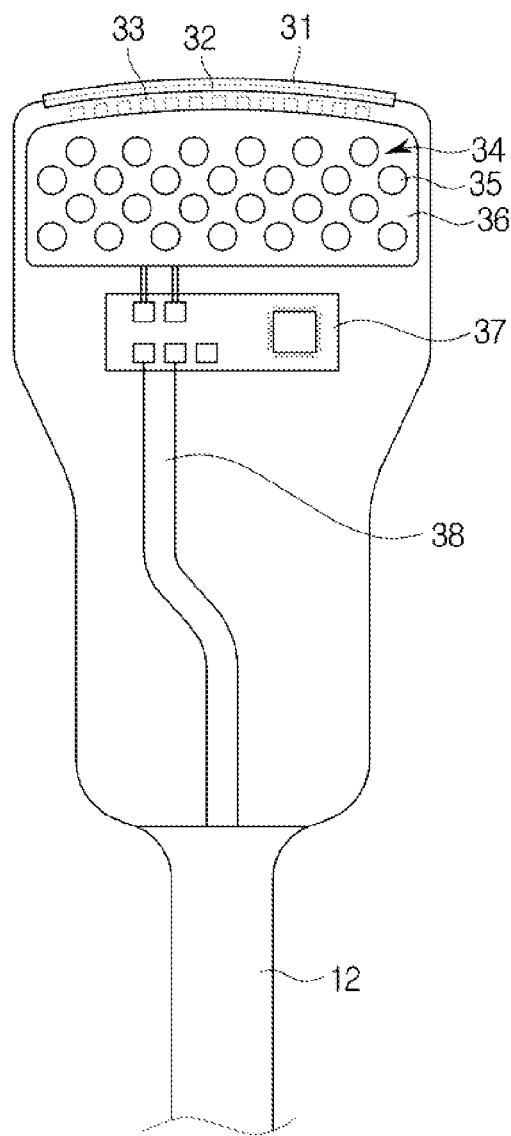
FIG. 31 illustrates a cross-sectional view of an embodiment of an ultrasonic probe.

FIG. 31 illustrates a cross-sectional view of an embodiment of the ultrasound probe 10. The ultrasound probe 10 may include, for example, an acoustic lens 31, an acoustic matching layer 32, an ultrasound transducer support 34, an ultrasound probe processor 37, and a wire 38.

The acoustic lens 31 may focus or irradiate sound or ultrasound. The acoustic lens 31 may have ultrasound generated from ultrasound transducers 33 focused on the target part ob1. The acoustic matching layer 32 may sustain straightness and intensity of ultrasound generated from the ultrasound transducers 33 or may minimize the ultrasound being reflected from an external medium.

The ultrasound transducers 33 may generate or receive ultrasound. Specifically, the ultrasound transducers 33, may generate ultrasound by converting alternate current (AC) energy with a certain frequency to mechanical vibration with the same frequency, or convert mechanical vibration with a certain frequency to AC energy. When the ultrasound transducers 33 are supplied AC power from e.g., a battery, piezoelectric resonators or thin films of the ultrasound transducers 33 vibrate, causing to generate ultrasound. The ultrasound generated from the ultrasound transducers 33 may be irradiated into the object ob. The ultrasound may be focused on at least one target part ob1 inside the object ob. In this regard, the ultrasound may be focused on a single spot (single focusing) or on multiple spots (multi-focusing). The ultrasound transducer may include at least one of a piezoelectric ultrasound transducer that utilizes a piezoelectric effect of a piezoelectric material, a magnetostrictive ultrasound transducer that uses a magnetostrictive effect of a magnetic substance to convert wave energy and electric energy, and Capacitive Micromachined Ultrasound Transducer (CMUT) that transmits or receives ultrasound using vibration of hundreds or thousands of micromachined thin films. In addition, the ultrasound transducers 33 may include any other type of transducers that generate ultrasound based on electrical signals or generate electrical signals based on ultrasound. The ultrasound transducers 33 may be mounted on a face of the ultrasound transducer support 34.

The ultrasound transducer support 34 may absorb part of the ultrasound generated from the ultrasound transducers 33 or release heat while supporting the ultrasound transducers 33. The ultrasound transducer support 34 may include sound absorbent materials 35 and heat transfer materials 36. As described with reference to FIGS. 1 to 28, the ultrasound transducer support 34 may include multiple layers. The arrangement pattern of sound absorbent materials of a first layer is symmetrical to that of a second layer. In other words, in the second layer, sound absorbent materials may be arranged in at least one area that corresponds to where heat transfer materials are arranged in the first layer; and heat transfer materials may be arranged in at least one area that corresponds to where sound absorbent materials are arranged in the first layer. Any other layer, e.g., a third layer may have the same arrangement pattern as in the first layer or the second layer.

The ultrasound probe processor 37 may generate control signals to control overall operations of the ultrasound probe 10. The ultrasound probe processor 37 may also amplify ultrasound signals irradiated from the ultrasound transducers 33 or convert the analog ultrasound signals to digital signals. The ultrasound probe processor 37 may be implemented with various semiconductor chips and printed circuit boards (PCB). The semiconductor chips may include memory or non-memory semiconductors. The ultrasound probe processor 37 may be mounted on the rear face of the ultrasound transducer support 34 as shown in FIG. 31, or on a side of the ultrasonic transducer support 34. In addition, the ultrasound probe processor 37 may be mounted any place inside the housing of the ultrasound probe 10.

The wire 38 may serve as a path for delivering ultrasound signals to the main body 20. The wire 38 may be a part of a connection cable 12.

Figure 32:
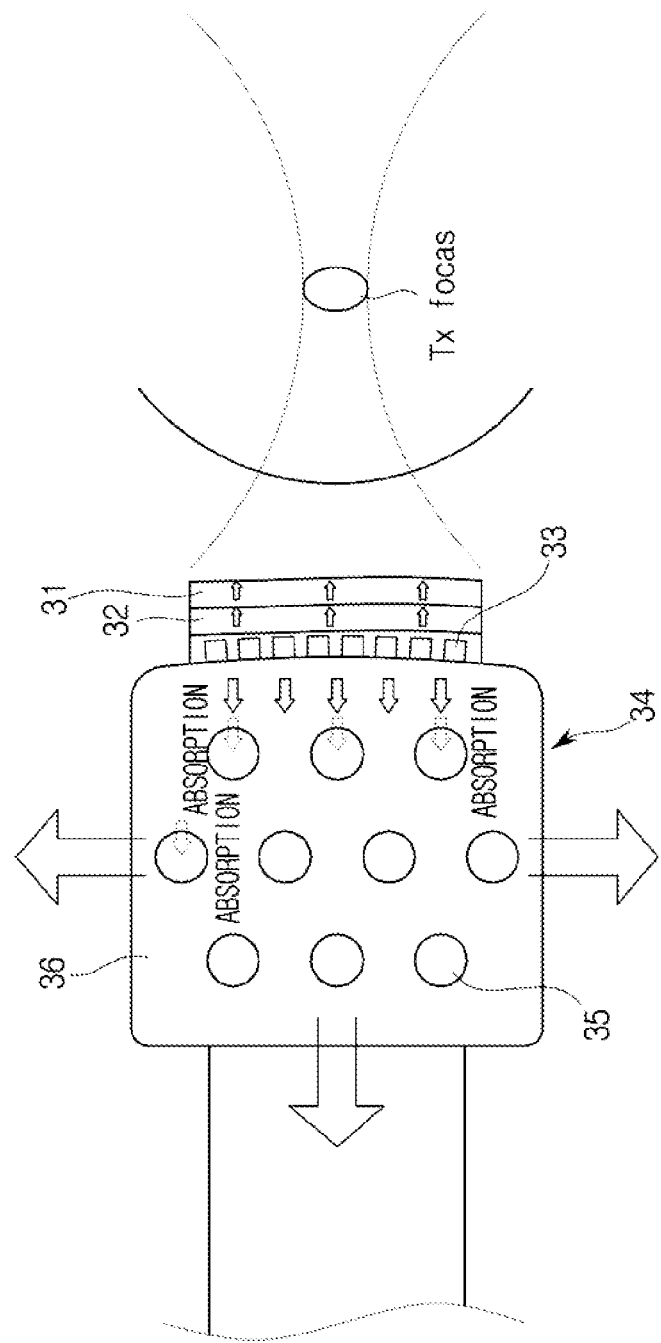
FIG. 32 illustrates how an ultrasound probe irradiates ultrasound.
Figure 33:
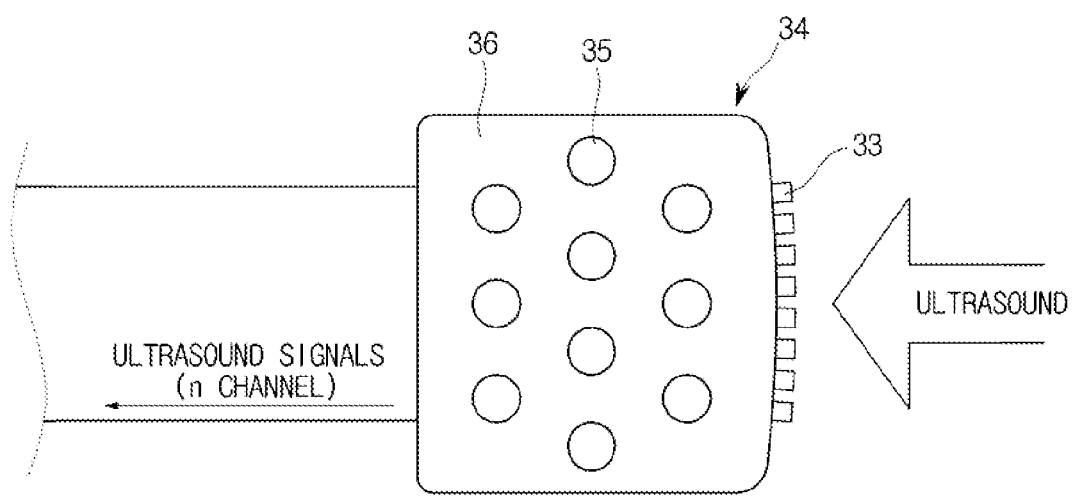
FIG. 33 illustrates how an ultrasound probe receives ultrasound.

FIG. 32 illustrates how an ultrasound probe irradiates ultrasound, and FIG. 33 illustrates how an ultrasound probe receives ultrasound. Referring to FIG. 32, the ultrasound probe transducer 33 may generate ultrasound with a certain frequency based on applied power. The generated ultrasound may be focused by the acoustic lens 31 and the acoustic matching layer 32 on a target part of an object with a predetermined focus size. Ultrasound generated from the ultrasound transducers 33 may be irradiated not only toward the object ob but also toward the ultrasonic transducer support 34. Sound absorbent materials of the ultrasound transducer support 34 may avoid the ultrasound irradiated toward the ultrasonic transducer support 34 being transmitted to any other faces of the ultrasound transducer support 34 by absorbing the ultrasound. Also, heat generated when the ultrasound transducers 33 generate ultrasound may be transferred toward the ultrasound transducer support 34 and released to the outside of the ultrasound transducer support 34. The ultrasound irradiated toward the object ob may be reflected from the target part ob1, and the ultrasound transducers 33 may receive the reflected ultrasound, convert it to multi-channel ultrasound signals, and send the multi-channel ultrasound signals to a beam forming unit 21.

The ultrasound probe 10 and the main body 20 are coupled to each other with the connection cable 12. One end of the connection cable 12 may be coupled with the ultrasonic probe 10 and the other end may be coupled with the main body 12. At the other end of the connection cable 12, a connector 11 that may be connected to or removed from a slot arranged on the main body's 20 side may be arranged. Ultrasound caught by the ultrasound probe 10 may be delivered to the main body 20 through the connection cable 12. In some embodiments, beamformed ultrasound may be delivered to the main body 20 through the connection cable 12. In a case where the ultrasound probe 10 and the main body 20 each include a wireless communication module including e.g., a wireless communication chip and an antenna for data communication, the connection cable 12 may be omitted.

With the ultrasound, the main body 20 may create an ultrasound image or control general operations of the ultrasound imaging apparatus M. Referring to FIG. 30, the main body 20 may include, for example, a beamforming unit 21, an image processing unit 22, a storage 23, a display 24, an input unit 25, a system controller 26, and an ultrasound generation controller 27. At least one of the components of the main body 20 may also be included in any other device, such as the ultrasonic probe 10 or associated workstation (not shown). The workstation may be connected to the main body 20 over a communication network. The beamforming unit 21, the image processing unit 22, the display 24, the input unit 25, the system controller 26, and the ultrasound generation controller 27 may be implemented by a central processing unit (CPU) or graphic processing unit (GPU) included in the ultrasonic probe 10, the main body 20, or the workstation. The CPU and the GPU may be implemented with semiconductor chips and PCBs. The storage 23 may be implemented by e.g., a semiconductor memory device or magnetic disc memory device included in the ultrasound probe 10, the main body 20, or the workstation.

Figure 34:
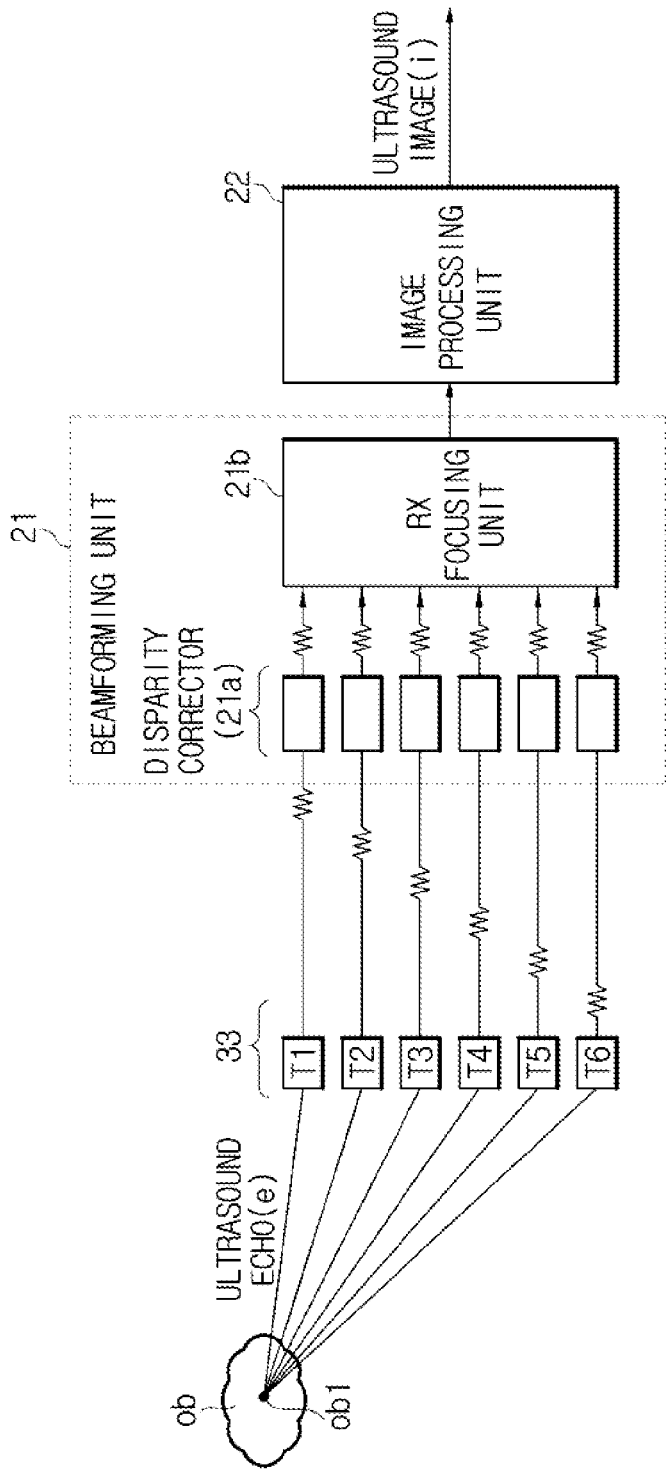
FIG. 34 is a block diagram of an embodiment of a beamforming unit and an image processing unit.

FIG. 34 is a block diagram of an embodiment of a beamforming unit and an image processing unit. Referring to FIG. 34, ultrasound caught by the ultrasound transducers 33 may be delivered to the beamforming unit 21. The beamforming unit 21 may include a disparity corrector 21*a* and receiver (RX) focusing unit 21*b*. The disparity corrector 21*a* may correct a time difference (channel delay) between multiple ultrasound signals output from the ultrasound transducers 33. Specifically, the disparity corrector 21*a* may output disparity-corrected ultrasound signals by delaying the ultrasound output on multiple channels of ultrasound transducers T1 to T6 by a predetermined time. Accordingly, ultrasonic echoes reflected from the same target part at the same time t may reach RX focusing unit 21*b* simultaneously. The RX focusing unit 21*b* may obtain and output beamformed ultrasound signals by focusing the disparity-corrected ultrasound signals. In an embodiment, the RX focusing unit 21*b* may focus signals on multiple channels by accentuating or attenuating signals on the channels by imposing a predetermined weight, a beamforming coefficient on the ultrasound signal on each channel. The beamforming coefficient may be determined independently from the ultrasound signal on each channel (data-independent beamforming) or may be determined depending on the ultrasound signal on each channel (data-dependent beamforming). The beamformed ultrasound signals may be delivered to the image processing unit 22.

Figure 35:
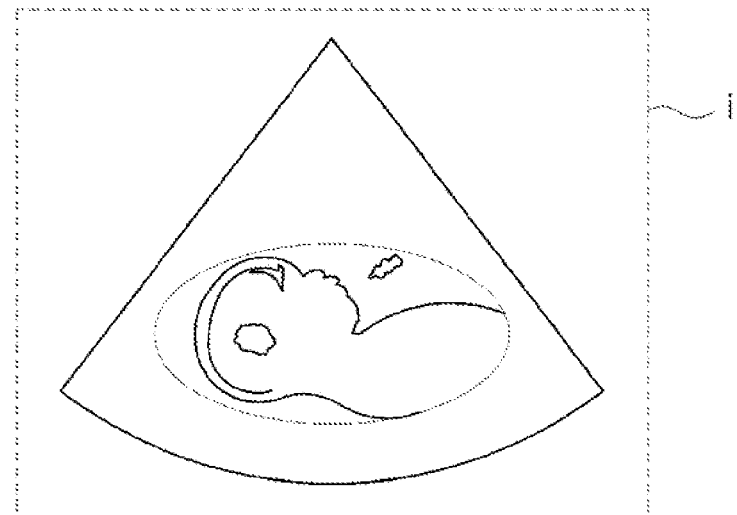
FIG. 35 illustrates an exemplary ultrasound image.

The image processing unit 22 may create an ultrasound image with the beamformed ultrasound signals. The image processing unit 22 may create an ultrasound image using scan conversion. The ultrasound image may be an A mode, B mode, or M mode ultrasound image. The A mode ultrasound image refers to an ultrasound image made by utilizing amplitude to image an integrity of reflection from a target spot t1 based on the reflection time or the distance between the target spot t1 and the ultrasound probe 10. FIG. 35 illustrates an exemplary ultrasound image. The B mode ultrasound image refers to an ultrasound image resulting from the magnitude of the ultrasound being imaged using the brightness. The B mode ultrasound image gives an advantage for a user, such as a doctor or a patient to readily recognize an internal condition of the object. The M mode ultrasound image refers to an ultrasound image resulting from an amount of a change in motion of the object being imaged. In addition, the ultrasound image may include a Doppler image formed by using the Doppler effect. The image processing unit 22 may also correct the ultrasound image. Correction of the ultrasound image may be performed according to the user's intention or a predefined setting. The image processing unit 22 may correct brightness, luminosity, sharpness, contrast, color or the like of an entire or a part of the ultrasound image in order for the user to clearly view tissues in the ultrasound image. The image processing unit 22 may create a three dimensional (3D) ultrasound image using volume data. The image processing unit 22 may store the generated or corrected ultrasound image in the storage 23 or display them on the display 24.

The storage 23 may store the ultrasound image temporarily or non-temporarily.

The storage 23 may be implemented by a storage device included in the main body 20 or workstation. The storage device may be a semiconductor storage device or a magnetic disc storage device.

The display 24 may present the ultrasound image for the user. The display 24 may use a plasma display panel (PDP), light emitting diodes (LED), a liquid crystal display (LCD), or the like. The LED may include organic light emitting diodes (OLEDs). The display 24 may also be a 3D display for representing stereographic images. The display 24 may also be a touch screen. In this case where the display 24 is a touch screen, the display 24 may serve as the input unit 25 as well. The display 24 may use a resistive touch screen panel or a capacitive touch screen panel. Furthermore, the display 24 may use ultrasound or infrared. In the case where the display 24 is a touch screen, the user may input various commands using a touch means, such as a finger or a touch pen.

The input unit 25 may receive various commands from the user in connection with control over the ultrasound imaging apparatus M. The input unit 25 may output electrical signals in accordance with user's manipulation, and send the electrical signals to the system controller 26. The input unit 25 may include at least one of e.g., keyboards, mice, trackballs, touch screens, touch pads, paddles, various levers, handles, joysticks, and other various input devices.

The system controller 26 may control overall operations of the ultrasound imaging apparatus M in accordance with commands of the user or predefined settings. The system controller 26 may generate a control command based on a frequency of ultrasound to be irradiated, and then send the control command to the ultrasound generation controller 27. The ultrasound generation controller 27 may determine a frequency or a magnitude of a current to be applied to the ultrasound generator 10*a* of the ultrasound probe 10 based on the received control command, and control the current with the determined frequency or magnitude to be applied to the ultrasound generator 10*a*.

While a general ultrasound imaging apparatus has been described as an embodiment of the ultrasound imaging apparatus M, any type of ultrasound imaging apparatus not described above or shown in the attached drawings may be used in other embodiments of the present disclosure. The ultrasound imaging apparatus M may be, for example, a vibroacoustography, picosecond ultrasonics, or a photoacoustic imaging apparatus. In addition, any type of ultrasound imaging apparatus that may catch ultrasound to obtain an image may be used as an example of the ultrasound imaging apparatus M.

According to the embodiments of the present disclosure, a transducer support may easily absorb ultrasound generated from ultrasound transducers and protect against heat due to the ultrasound, thereby increasing sound absorbing power and heat-resistance.

With the ultrasound probe device and ultrasound imaging apparatus using the transducer support, an ultrasound image may be obtained with reduced noise caused by ultrasound spreading in a direction opposite from the direction of transmission, and malfunction or disorder caused by e.g., overheating of the ultrasound probe device can be avoided.

Furthermore, the transducer support facilitates simplification of the manufacturing process, thereby providing economical effects, such as time and cost reduction in manufacturing the ultrasound probe device and ultrasound imaging apparatuses.

Several embodiments have been described in connection with e.g., ultrasound probes, but a person of ordinary skill in the art will understand and appreciate that various modifications can be made without departing the scope of the present disclosure. Thus, it will be apparent to those ordinary skilled in the art that the disclosure is not limited to the embodiments described, which have been provided only for illustrative purposes.

What is claimed is:

1. A transducer support comprising:
   a first layer comprising first areas in which heat transfer materials are arranged and second areas in which sound absorbent materials are arranged, wherein the first and second areas are arranged alternately; and a second layer comprising third areas located directly below the first areas in which sound absorbent materials are arranged and fourth areas located directly below the second areas in which heat transfer materials are arranged.

2. The transducer support of claim 1, further comprising:
a third layer comprising fifth areas located directly below the fourth areas in which sound the absorbent materials are arranged.

3. The transducer support of claim 1, wherein the second layer further comprises sixth areas located directly below the first areas in which the heat transfer materials are arranged.

4. The transducer support of claim 3, further comprising:
a third layer comprising seventh areas located directly below the sixth areas in which sound absorbent materials are arranged.

5. The transducer support of claim 1, wherein at least one of the first and second layers comprise the heat transfer materials and the sound absorbent materials arranged in multiple columns.

6. The transducer support of claim 5, wherein the multiple columns comprise a first column in which heat transfer materials and sound absorbent materials are arranged alternately; and a second column in which a sound absorbent material is placed next to a heat transfer material of the first column and a heat transfer material is placed next to a sound absorbent material of the first column.

7. The transducer support of claim 1, further comprising:
a fourth layer located between the first layer and the second layer, the fourth layer including a heat transfer material.

8. The transducer support of claim 1, wherein the sound absorbent materials are formed in the shape of at least one of a polyhedron, a cylinder, and a cone.

9. The transducer support of claim 1, wherein the sound absorbent materials comprise at least one of epoxy and hafnium oxides.

10. The transducer support of claim 1, wherein the heat transfer materials comprise at least one of graphite, tungsten, tungsten oxide, silicon, aluminum oxide, and glass micro balloon filter.

11. A transducer support comprising:
a first layer in which heat transfer materials and sound absorbent materials are arranged alternately; and
a second layer having sound absorbent materials arranged in all or some of areas corresponding to where the heat transfer materials of the first layer are arranged and heat transfer materials arranged in areas corresponding to where the sound absorbent materials of the first layer are arranged.

12. The transducer support of claim 11, further comprising:
a third layer having heat transfer materials arranged in all or some of areas corresponding to where the heat transfer materials of the first layer are arranged and sound absorbent materials arranged in all or some of areas corresponding to where the sound absorbent materials of the first layer are arranged.

13. A transducer support comprising:
a main body that transfers heat and includes first and second layers; and
a plurality of sound absorbent materials arranged in each of the first and second layers, wherein the plurality of sound absorbent materials are arranged in the first layer in a first pattern and the plurality of sound absorbent materials are arranged in the second layer in a second pattern opposite to the first pattern.

14. The transducer support of claim 13, further comprising:
a third layer having the plurality of sound absorbent materials arranged in the same pattern as in the first layer.

15. An ultrasound probe comprising:
at least one ultrasound transducer; and
an ultrasound transducer support on one side of which the at least one ultrasound transducer is mounted,
wherein the ultrasound transducer support comprises;
a first layer having first areas in which heat transfer materials are arranged and second areas in which sound absorbent materials are arranged, the first and second areas being arranged alternately; and
a second layer having third areas located directly below the first areas in which sound absorbent materials are arranged and fourth areas located directly below the second areas in which heat transfer materials are arranged.

16. The ultrasound probe of claim 15, further comprising:
a third layer having fifth areas located directly below the fourth areas in which sound absorbent materials are arranged.

17. The ultrasound probe of claim 15, wherein the second layer further comprises: sixth areas located directly below the first areas in which heat transfer materials are arranged.

18. The ultrasound probe of claim 17, further comprising:
a third layer having seventh areas located directly below the sixth areas in which sound absorbent materials are arranged.

19. The ultrasound probe of claim 15, wherein at least one of the first and second layers has the heat transfer materials and the sound absorbent materials arranged in multiple columns.

20. The ultrasound probe of claim 19, wherein the multiple columns comprise a first column in which heat transfer materials and sound absorbent materials are arranged alternately; and a second column in which a sound absorbent material is placed next to a heat transfer material of the first column and a heat transfer material is placed next to a sound absorbent material of the first column.

21. The ultrasound probe of claim 15, further comprising:
a fourth layer located between the first layer and the second layer, the fourth layer including a heat transfer material.

22. The ultrasound probe of claim 15, wherein the sound absorbent materials are in the shape of at least one of a polyhedron, a cylinder, and a cone.

23. The ultrasound probe of claim 15, wherein the sound absorbent materials include at least one of epoxy and hafnium oxides.

24. The ultrasound probe of claim 15, wherein the heat transfer materials include at least one of graphite, tungsten, tungsten oxide, silicon, aluminum oxide, and glass micro balloon filter.

25. An ultrasound imaging apparatus comprising:
an ultrasound probe configured to catch ultrasound and output an ultrasound signal corresponding to the ultrasound; and
a main body configured to generate an ultrasound image with the ultrasound signal output from the ultrasound probe,
wherein the ultrasound probe includes at least one ultrasound transducer and an ultrasound transducer support on one side of which the at least one ultrasound transducer is mounted, and
wherein the ultrasound transducer support comprises;

a first layer having first areas in which heat transfer materials are arranged and second areas in which sound absorbent materials are arranged, the first and second areas being arranged alternately; and a second layer having third areas located below the first areas in which sound absorbent materials are arranged and fourth areas located below the second areas in which heat transfer materials are arranged.

26. A transducer support partitioned into multiple layers, the transducer support comprising:

a first layer alternately comprised of first areas in which sound absorbent materials are arranged and second areas in which heat transfer materials are arranged;

a second layer alternately comprised of third areas in which sound absorbent materials are arranged and fourth areas in which heat transfer materials are arranged;

wherein the locations of the first areas in the first layer correspond with the locations of the fourth areas in the second layer and the locations of the second areas in the first layer correspond with the locations of the third area in the second layer.

27. A transducer support partitioned into multiple layers, the transducer support comprising:

a first layer alternately comprised of first areas in which sound absorbent materials are arranged and second areas in which heat transfer materials are arranged;

a second layer alternately comprised of third areas in which sound absorbent materials are arranged and fourth areas in which heat transfer materials are arranged;

wherein the locations of the first areas in the first layer are disposed directly above the locations of the fourth areas in the second layer and the locations of the second areas in the first layer are disposed directly above the locations of the third area in the second layer.

* * * * *

UNITED STATES PATENT AND TRADEMARK OFFICE
CERTIFICATE OF CORRECTION

PATENT NO. : 9,858,911 B2
APPLICATION NO. : 14/511511
DATED : January 2, 2018
INVENTOR(S) : Chang Yeon Won et al.

It is certified that error appears in the above-identified patent and that said Letters Patent is hereby corrected as shown below:

On the Title Page

Item [72] (Inventors), Line 11:
Delete "Jeong Mln Na," and insert -- Jeong Min Na, --, therefore.

Signed and Sealed this
Twenty-ninth Day of May, 2018

Andrei Iancu
*Director of the United States Patent and Trademark Office*